US009566365B2

(12) United States Patent
Kaplan et al.

(10) Patent No.: US 9,566,365 B2
(45) Date of Patent: Feb. 14, 2017

(54) SILK FIBROIN AND POLYETHYLENE GLYCOL-BASED BIOMATERIALS

(75) Inventors: David L. Kaplan, Concord, MA (US); Monica A. Serban, Melrose, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 13/820,440

(22) PCT Filed: Sep. 1, 2011

(86) PCT No.: PCT/US2011/050238
§ 371 (c)(1),
(2), (4) Date: Jul. 17, 2013

(87) PCT Pub. No.: WO2012/031144
PCT Pub. Date: Mar. 8, 2012

(65) Prior Publication Data
US 2013/0287742 A1     Oct. 31, 2013

Related U.S. Application Data

(60) Provisional application No. 61/379,065, filed on Sep. 1, 2010.

(51) Int. Cl.
| A61L 24/10 | (2006.01) |
| C08L 77/04 | (2006.01) |
| C08L 71/02 | (2006.01) |
| C08L 89/00 | (2006.01) |
| A61L 27/26 | (2006.01) |
| A61L 27/52 | (2006.01) |
| A61L 27/54 | (2006.01) |
| A61L 24/00 | (2006.01) |

(52) U.S. Cl.
CPC .......... *A61L 24/108* (2013.01); *A61L 24/0094* (2013.01); *A61L 27/26* (2013.01); *A61L 27/52* (2013.01); *A61L 27/54* (2013.01); *C08L 71/02* (2013.01); *C08L 77/04* (2013.01); *C08L 89/00* (2013.01); *A61L 2300/406* (2013.01)

(58) Field of Classification Search
CPC .... A61L 24/0094; A61L 24/108; A61L 27/26; A61L 27/52; A61L 27/54; A61L 2300/406; C08L 71/02; C08L 77/04; C08L 89/00
USPC .. 424/484; 514/772.1, 772.3, 782; 525/54.1, 408
See application file for complete search history.

(56) References Cited

U.S. PATENT DOCUMENTS

| 1,989,005 | A | 1/1935 | Fink et al. |
| 4,233,212 | A | 11/1980 | Otoi et al. |
| 4,818,291 | A | 4/1989 | Iwatsuki et al. |
| 4,820,418 | A | 4/1989 | Hirotsu et al. |
| 5,047,507 | A | 9/1991 | Buchegger et al. |
| 5,290,494 | A | 3/1994 | Coombes et al. |
| 5,606,019 | A | 2/1997 | Cappello |
| 5,728,810 | A | 3/1998 | Lewis et al. |
| 5,770,193 | A | 6/1998 | Vacanti et al. |
| 5,994,099 | A | 11/1999 | Lewis et al. |
| 6,110,590 | A | 8/2000 | Zarkoob et al. |
| 6,123,819 | A | 9/2000 | Peeters |
| 6,175,053 | B1 | 1/2001 | Tsubouchi |
| 6,592,623 | B1 | 7/2003 | Bowlin et al. |
| 6,815,427 | B2 | 11/2004 | Tsubouchi et al. |
| 6,902,932 | B2 | 6/2005 | Altman et al. |
| 7,041,797 | B2 | 5/2006 | Vollrath |
| 7,057,023 | B2 | 6/2006 | Islam et al. |
| 7,285,637 | B2 | 10/2007 | Armato et al. |
| 7,635,755 | B2 | 12/2009 | Kaplan et al. |
| 7,662,409 | B2 | 2/2010 | Masters |
| 7,674,882 | B2 | 3/2010 | Kaplan et al. |
| 7,727,575 | B2 | 6/2010 | Kaplan et al. |
| 7,842,780 | B2 | 11/2010 | Kaplan et al. |
| 7,960,509 | B2 | 6/2011 | Kaplan et al. |
| 8,071,722 | B2 | 12/2011 | Kaplan et al. |
| 2002/0028243 | A1 | 3/2002 | Masters |

(Continued)

FOREIGN PATENT DOCUMENTS

| CA | 2405850 | 10/2002 |
| EP | 1440088 | 5/2008 |

(Continued)

OTHER PUBLICATIONS

Agarwal et al., Journal of Applied Polymer Science, 63(3):401-410 (1997). "Effect of Moisture Absorption on the Thermal Properties of Bombyx mori Silk Fibroin Films."

Altman et al., Biomaterials, 24:401-416 (2003). "Silk-based biomaterials."

Ando et al, Reports on Progress in Polymer Physics in Japan, XXIII:775-778 (1980). "Piezoelectric and Related properties of Hydrated Silk Fibroin."

(Continued)

*Primary Examiner* — Robert Jones, Jr.
(74) *Attorney, Agent, or Firm* — Choate, Hall & Stewart, LLP

(57) ABSTRACT

This invention relates to methods and compositions for preparation of silk-PEGs based biomaterials through cross-linking by chemically reacting active polyethylene glycols (PEGs) possessing different chemical groups (e.g., thiols and maleimides functionalized PEGs) that are additionally stabilized by the beta-sheet formation of silk fibroin. The crosslinked silk-PEGs biomaterials present strong adhesive properties, which are comparable to or better than the current leading PEG-based sealant, depending on the silk concentration in the silk-PEGs biomaterials. In addition, the silk-PEGs based biomaterials are cytocompatible, show decreased swelling behavior and longer degradation times, which make them suitable for hemostatic applications where the current available tissue sealant products can be contraindicated.

21 Claims, 18 Drawing Sheets

(56) References Cited

U.S. PATENT DOCUMENTS

| | | |
|---|---|---|
| 2003/0007991 A1 | 1/2003 | Masters |
| 2003/0183978 A1 | 10/2003 | Asakura |
| 2004/0005363 A1 | 1/2004 | Tsukada et al. |
| 2004/0266992 A1 | 12/2004 | Migliaresi et al. |
| 2005/0260706 A1 | 11/2005 | Kaplan et al. |
| 2007/0187862 A1 | 8/2007 | Kaplan et al. |
| 2007/0212730 A1 | 9/2007 | Vepari et al. |
| 2008/0085272 A1 | 4/2008 | Kaplan et al. |
| 2008/0131509 A1 | 6/2008 | Hossainy et al. |
| 2008/0293919 A1 | 11/2008 | Kaplan et al. |
| 2009/0171467 A1 | 7/2009 | Mann et al. |
| 2009/0202614 A1 | 8/2009 | Kaplan et al. |
| 2009/0232963 A1 | 9/2009 | Kaplan et al. |
| 2009/0234026 A1 | 9/2009 | Kaplan et al. |
| 2009/0297588 A1 | 12/2009 | Rheinnecker et al. |
| 2010/0028451 A1 | 2/2010 | Kaplan et al. |
| 2010/0046902 A1 | 2/2010 | Kaplan et al. |
| 2010/0055438 A1 | 3/2010 | Kaplan et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0095827 A1 | 4/2010 | Rheinnecker et al. |
| 2010/0096763 A1 | 4/2010 | Kaplan et al. |
| 2010/0120116 A1 | 5/2010 | Kaplan et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0292338 A1 | 11/2010 | Rheinnecker et al. |
| 2011/0014263 A1* | 1/2011 | Altman .............. A61K 38/1767 424/423 |
| 2011/0046686 A1 | 2/2011 | Kaplan et al. |
| 2011/0076384 A1 | 3/2011 | Cannizzaro et al. |
| 2011/0121485 A1 | 5/2011 | Rheinnecker et al. |
| 2011/0135697 A1 | 6/2011 | Omenetto et al. |
| 2011/0152214 A1 | 6/2011 | Boison et al. |
| 2011/0171239 A1 | 7/2011 | Kaplan et al. |
| 2012/0121820 A1 | 5/2012 | Kaplan et al. |
| 2012/0123519 A1 | 5/2012 | Lovett et al. |

FOREIGN PATENT DOCUMENTS

| | | |
|---|---|---|
| GB | 1182153 | 2/1970 |
| JP | 55-139427 | 10/1980 |
| JP | 56166235 | 12/1981 |
| JP | 58-38449 | 8/1983 |
| JP | 60-142259 | 7/1985 |
| JP | 60-259677 | 12/1985 |
| JP | S64-85272 A | 3/1989 |
| JP | 01118544 | 11/1989 |
| JP | 04-263611 | 9/1992 |
| JP | 06-346314 | 12/1994 |
| JP | 08-295697 | 11/1996 |
| JP | 10-36676 | 2/1998 |
| JP | 2000-273264 | 10/2000 |
| JP | 2003192807 | 7/2003 |
| JP | 2004068161 | 3/2004 |
| JP | 2006-504450 A | 2/2006 |
| JP | 2010-511426 A | 4/2010 |
| WO | 99/01089 | 1/1999 |
| WO | 01/36531 | 5/2001 |
| WO | 01/56626 | 8/2001 |
| WO | 02/072931 | 9/2002 |
| WO | 03/022909 | 3/2003 |
| WO | 03/038033 | 5/2003 |
| WO | 2004/000915 | 12/2003 |
| WO | 2004000915 A2 | 12/2003 |
| WO | 2004/041845 | 5/2004 |
| WO | 2005/012606 | 2/2005 |
| WO | 2005/123114 | 12/2005 |
| WO | 2008/127405 | 10/2008 |
| WO | 2009/156226 | 12/2009 |
| WO | 2010057142 A2 | 5/2010 |
| WO | 2011/006133 | 1/2011 |
| WO | WO-2012/031144 A2 | 3/2012 |

OTHER PUBLICATIONS

Asakura et al., Macromolecules, 17:1075-1081 (1984). NMR of silk fibroin 2. 13C NMR study of the chain dynamics and solution structure of Bombyx mori silk fibroin.

Asakura et al., Macromolecules, 18:1841-1845 (1985). "Conformation characterization of Bombyx mori silk fibroin in the solid state by high-frequency 13C cross polarization-magic angle spinning NMR, X-ray diffraction and infrared spectroscopy."

Chen et al., J Appl Polymer Sci, 65:2257-2262 (1997). "pH sensitivity and ion sensitivity of hydrogels based on complex-forming chitosan/silk fibroin interpenetrating polymer network."

Chen et al., J Appl Polymer Sci, 73:975-980 (1999). "Separation of alcohol-water mixture by pervaporation through a novel natural polymer blend membrane-chitosan/silk fibroin blend membrane."

Chen et al., Proteins: Structure, Function, and Bioinformatics, 68:223-231 (2007). "Conformation transition kinetics of Bombyx mori silk protein."

Demura et al., Biosensors, 4:361-372 (1989). "Immobilization of biocatalysts with Bombyx mori silk fibroin by several kinds of physical treatment and its application to glucose sensors."

Demura et al., J Membrane Science, 59:39-52 (1991). "Porous membrane of Bombyx mori silk fibroin: structure characterization, physical properties and application to glucose oxidase immobilization."

Derwent Record, Abstract of JP 08295697 A2 "Production of aqueous solution of silk fibroin at high concentration." Nov. 12, 1996.

Doshi et al. J Electrostatics, 35:151-160 (1995). "Electrospinning process and applications of electrospun fibers."

Freddi et al., J Appl Polymer Sci, 56:1537-1545 (1995). "Silk fibroin/cellulose blend films: preparation, structure, and physical properties."

Hijirida et al., Biophysical Journal, 71:3442-3447 (1996). "13C NMR of Nephila clavipes major ampullate silk gland."

Hinman et al., TIBTECH, 18:374-379 (2000). "Synthetic spider silk: a modular fiber."

Horan et al., Biomaterials, 26:3385-3393 (2005). "In vitro degradation of silk fibroin."

Hu et al., Biomacromolecules, 12:1686-1696 (2011). "Regulation of Silk Material Structure by Temperature-Controlled Water Vapor Annealing."

Huang et al., J Biomater Sci Polymer Edn, 12(9):979-993 (2001). "Engineered collagen-PEO nanofibers and fabrics."

Huang et al., Macromolecules, 33:2989-2997 (2000). "Generation of synthetic elastin-mimetic small diameter fibers and fiber networks."

Jin et al., Biomacromolecules, 3:1233-1239 (2002). "Electrospinning Bombyx mori silk with poly(ethylene oxide)."

Jin et al., Adv. Funct. Mater., 15:1241-1247 (2005). "Water-Stable Silk Films with Reduced β-Sheet Content."

Jin et al., Nature, 424:1057-1061 (2003). "Mechanism of silk processing in insects and spiders."

Kim et al., Biomacromolecules, 5:786-792 (2004). "Structure and Properties of Silk Hydrogels."

Kweon et al., J Appl Polymer Sci, 80:1848-1853 (2001). "Preparation of semi-interpenetrating polymer networks composed of silk fibroin and poly(ethylene glycol) macromer."

Lazaris, Science, 295:472-476 (2002). "Spider silk fibers spun from soluble recombinant silk produced in mammalian cells."

Li et al., Biomaterials, 27:3115-3124 (2006). "Electrospun Silk-BMP-2 scaffolds for bone tissue engineering."

Liang et al., J Appl Polymer Sci, 45:1937-1943 (1992). "Improvements of the physical properties of fibroin membranes with sodium alginate."

Lu et al., Biomacromolecules, 10:1032-1042 (2009). "Stabilization of Enzymes in Silk Films."

(56) References Cited

OTHER PUBLICATIONS

Lu et al., Acta Biomater. 6(4):1380-1387 (2010). "Water-Insoluble Silk Films with Silk I Structure."
Megeed et al., Pharmaceutical Research, 19(7):954-959 (2002). "Controlled release of plasmid DNA from a genetically engineered silk-elastinlike hydrogel."
Nazarov et al., Biomacromolecules, 5:718-726 (2004). "Porous 3-D Scaffolds from Regenerated Silk Fibroin."
Petrini et al., Journal of Materials Science: Materials in Medicine, 12:849-853 (2001). "Silk fibroin-polyurethane scaffolds for tissue engineering."
Reneker et al., Nanotechnology, 7:216-223 (1996). "Nanometre diameter fibres of polymer, produced by electrospinning."
Sawyer et al., JAMA, 191(9):740-742 (1965). "Dextran therapy in thrombophlebitis." Abstract.
Sofia et al., Journal of Biomedical Materials Research, 54(1):139-148 (2001). "Functionalized silk-based biomaterials for bone formation."
U.S. Appl. No. 60/906,509, filed Mar. 13, 2007 by Omenetto et al.
U.S. Appl. No. 61/224,618, filed Jul. 10, 2009 by Numata et al.
Wang et al., Langmuir, 21:11335-11341 (2005). "Biomaterial coatings by stepwise deposition of silk fibroin."
Wenk et al., Diss. Eth No. 18659 (2009). "Silk Fibroin as a Vehicle for Drug Delivery in Tissue Regeneration."
Wilson et al., PNAS, 98(24):13660-13664 (2001). "Surface organization and nanopatterning of collagen by dip-pen nanolithography."
Yamada et al., Thin Solid Films, 440:208-216 (2003). "AFM observation of silk fibroin on mica substrates: morphologies reflecting the secondary structures."
Zhou et al., Chem Commun, 2518-2519 (2001). "Preparation of a novel core-shell nanostructured gold colloid-silk fibroin bioconjugate by the protein in situ redox technique at room temperature."
Gotoh et al., "Synthesis of poly{ethylene glycol}-silk fibroin conjugates and surface interaction between L-929 cells and the conjugates", Biomaterials 18(3):267-271 (1997).
International Search Report for PCT/US2011/050238, 4 pages (Apr. 26, 2012).
Written Opinion for PCT/US2011/050238, 6 pages (Apr. 26, 2012).
Extended European Search Report for EP 11822680.2, 6 pages (Jul. 11, 2014).
Smeenk, J.M. et al., Controlled assembly of macromolecular beta-sheet fibrils, Angew Chem. Int. Ed. Engl., 44(13):1968-71 (2005).

* cited by examiner

SILK FIBROIN AND POLYETHYLENE GLYCOL-BASED BIOMATERIALS

CROSS-REFERENCE TO RELATED APPLICATIONS

This application is a 35 U.S.C. §371 National Stage Entry Application of International Application No. PCT/US2011/050238, filed Sep. 1, 2011, which designates the U.S., and which claims benefit under 35 U.S.C. §119(e) of U.S. Provisional Application No. 61/379,065, filed Sep. 1, 2010, the content of which is incorporated herein by reference in its entirety.

GOVERNMENT SUPPORT

This invention was made with government support under grant No. P41 EB002520, awarded by the National Institutes of Health (Tissue Engineering Resource Center). The U.S. government has certain rights in the invention.

FIELD OF THE INVENTION

The invention relates to methods and compositions for preparing silk-PEGs crosslinked biomaterials. The silk-PEGs based biomaterials have desirable biological, physical and mechanical properties to be used as tissue sealant and hemostats.

BACKGROUND OF THE INVENTION

Hemostasis is a complex process which causes the bleeding process to stop. Hemostasis typically can be achieved by mechanical tamponade, e.g., mechanical agents for blockage of a break, blood cloth formation or artificial wound closure. Wheat & Wolf, 36 Urol. Clin. North Am. 265-75 (2009). For instance, mechanical agents, available as sponges, foams or powders of gelatin, collagen, cellulose or other polysaccharide, achieve hemostasis through mechanical tamponade, by swelling at the site of bleeding and molding to the wound shape. Spotnitz & Burks, 48 Transfusion 1502-16 (2008). When these materials are applied to the wound site, platelet stimulation, aggregation, degranulation and release of clotting factors can also occur. Jenkins et al., 132 J. Am. Med. Assoc. 124-32 (1946).

Blood clot formation can be initiated or achieved enzymatically by the use of thrombin, either alone or in combination with mechanical agents (e.g., bovine collagen sponges or porcine gelatin matrix) or fibrin sealants. Spotnitz & Burks, 2008. Thrombin acts by activating platelets at the site of injury and by cleaving fibrinogen to fibrin. Fibrin, in turn, crosslinks into an insoluble network where platelets adhere and form the homeostatic plug. When thrombin and mechanical agents are used in combination, they can act synergistically to stop blood loss. Gill et al., 65 Urology 463-66 (2005). For example, fibrin sealants, which are formulated as mixtures of thrombin and fibrinogen, can recapitulate the last step of the coagulation cascade and exogenously supply the material needed for the formation of the blood cloth. Lowe et al., 48 J. Cardiovasc. Surg. 323-31 (2007).

Hemostasis can also be attained by using reagents that self-crosslink while simultaneously covalently binding the adjacent tissues to physically close the wound site. For example, cyanoacrylate-based adhesives can rapidly polymerize in situ in the presence of endogenous hydroxyl groups through an exothermic reaction. Wheat & Wolf, 2009; Gill et al., 2005; Lowe et al., 2007; Marcovich et al., 57 Urology 806-10 (2001). Another commercially available crosslinking sealant is bovine albumin and glutaraldehyde-based, where glutaraldehyde acts by linking amine groups of albumin to extracellular matrix proteins found at the wound site. Furst & Banerjee, 79 Ann. Thorac. Surg. 1522-29 (2005). Nevertheless, the presence of glutaraldehyde raises toxicity issues. Furst & Banerjee, 2005. Chemical crosslinking polyethylene glycol (PEG)-based sealants have also been used as hemostatic reagents. Preul et al., 107 J. Neurosurg. 642-50 (2007); Torchiana, 18 J. Cardiac. Surg. 504-06 (2003); Wallace et al., 58 J. Biomed. Mater. Res. 545-55 (2001). However, commercial available PEG-based sealants, such as COSEAL® possess certain drawbacks, including limited applicability at pressure sensitive areas.

Although a series of hemostatic agents and tissue adhesives/sealants have been FDA approved and are currently used in the medical practice, control of bleeding in the operating room still presents issue. The currently commercially available formulations still need improvement, for example, for longer degradation time, better adhesive properties, or decreased swelling for applications on certain tissues, such as areas sensitive to nerve compression. Therefore, there is still a need in the art to improve the overall material properties for tissue sealant/adhesive materials.

SUMMARY OF THE INVENTION

The invention relates to methods, compositions, and kits for preparation of silk-PEGs-based biomaterials through crosslinking by chemically reacting active polyethylene glycols (PEGs) possessing different chemical groups (e.g., PEGs containing thiol and maleimide functional groups) that are additionally stabilized through the beta-sheet formation of silk. The silk-PEGs based biomaterials have desirable biological, physical and mechanical properties to be used as sealant and hemostats. Furthermore, the formulation of the silk-PEGs based biomaterials can be tuned in terms of properties such as adhesive/tissue sealing properties and degradability to fabricate application-oriented material.

One aspect of the invention relates to a matrix-forming composition comprising at least three components including silk fibroin (e.g., at a concentration of at least about 10 wt %) and at least two functionally activated PEG components. The two functionally activated PEG components can react with one another to form a crosslinked matrix, and the matrix can be additionally stabilized by the beta-sheet formation of the silk fibroin. Typically the two PEG components are not pre-mixed before the formation of the matrix. In some embodiments, each of the PEG components can be blended with the silk fibroin (e.g., at a concentration of at least about 10 wt %) before the formation of the matrix.

One aspect of the invention relates to a method of preparing a crosslinked polymer matrix comprising the steps of admixing a matrix-forming composition and crosslinking the components of the composition to form a crosslinked polymer matrix. The composition comprises at least two functionally activated PEG components capable of reacting with one another to form a crosslinked matrix, and silk fibroin capable of forming beta-sheets to further stabilize the crosslinked matrix.

Another aspect of the invention relates to a crosslinked polymer matrix formed from mixing the matrix-forming composition. Thus, the crosslinked polymer matrix comprises at least two functionally activated PEG components that have reacted with one another to form a crosslinked matrix, and silk fibroin (e.g., at a concentration of at least about 10 wt %) having formed beta-sheets to stabilize the crosslinked matrix. In some embodiments of some aspects described herein, the crosslinked polymer matrix can be a hydrogel.

In some embodiments, the silk fibroin used for preparing a crosslinked polymer matrix can be depleted of sericin.

Each of the functionally-activated PEG components in the matrix-forming compositions or crosslinked polymer matrices can independently have any number of PEG polymer chains ("arms"), e.g., at least two-armed, at least three-armed, at least four-armed PEG, at least eight-armed PEG or more. In one embodiment, at least one PEG component is a four-armed PEG. In another embodiment, each PEG component is a four-armed PEG.

In some embodiments of the matrix-forming composition or the crosslinked polymer matrix described herein, at least one of the PEG components can be functionally activated with a maleimidyl group. In some embodiments, at least one of the PEG components can be functionally activated with a thiol group. In certain embodiments, one of the PEG components can be functionally-activated with a maleimidyl group, while another of the PEG components can be functionally activated with a thiol group. The number and/or types of functional groups on each arm of the PEG components can be the same or different.

The crosslinked polymer matrices described herein have various properties that can allow them to be used as a tissue sealant, a hemostat and/or a tissue adhesive. For example, some embodiments of the crosslinked polymer matrix described herein can swell less than 80 wt % of the initial weight of the crosslinked polymer matrix, e.g., when exposed to a physiological condition. In other embodiments, the crosslinked polymer matrix can retain its volume in a physiological condition for at least about 10 days, e.g., the crosslinked polymer matrix can retain its volume until occurrence of wound healing. In some embodiments, the crosslinked polymer matrix described herein can possess an adhesion strength of at least about 10 Pa. Depending on various applications, in some embodiments, the matrix-forming composition or crosslinked polymer matrix can further comprise an active agent or a hemostatic agent.

Yet another aspect of the invention relates to a method of forming a tissue sealant or adhesive on a target site of a subject, e.g., an implant, a tissue or an organ. The method comprises administering to the target site a composition comprising at least two functionally activated PEG components capable of reacting with one another to form a crosslinked matrix, and a silk fibroin (e.g., at a concentration of at least about 10 wt %) capable of forming beta-sheets to stabilize the crosslinked matrix; and mixing the composition to crosslink the components and form a tissue sealant or adhesive on the target site.

Kits including delivery devices used for delivering the compositions are also described herein. In some embodiments, the kit can include an injection device to deliver the matrix-forming composition to a treatment area in situ, in vivo, or ex vivo applications.

To clarify, the crosslinked polymer matrices described herein are different from those described in U.S. Patent Application No.: US 2008/0131509 (Hossainy et al.). The matrices described in Hossainy et al. are not formed from a composition comprising silk fibroin solution at a concentration of at least about 10 wt % or higher. More importantly, Hossainy et al. does not demonstrate the adhesion strength of their composite matrix, while the inventors herein have demonstrated that the crosslinked polymer matrices formed from a silk solution with a concentration of less than about 10 wt % (e.g., 5 wt %) performs significantly poorer than COSEAL®, a FDA-approved tissue sealant, but those formed from a silk concentration of at least about 10% or higher surprisingly perform comparable to, or even better than COSEAL® (see FIG. 7B).

BRIEF DESCRIPTION OF THE DRAWINGS

FIG. 1A shows a schematic representation of the two-step crosslinking process in the silk-PEG materials. The protein structures shown in the schemes were used for illustrative purposes and cannot represent the actual configuration of the silk fibroin. FIG. 1B shows a schematic representation of the silk-PEG gel formation process in accordance with one or more embodiments of the invention.

FIGS. 3A and 3B show cytocompatibility of PEG and silk-PEG based biomaterials after 48 hours cell culture, respectively. Most or all of the cells shown on the images were viable. Very few or no dead cells were detected in either the PEG or PEG-silk-based biomaterials.

FIG. 4A shows the swelling profile of the silk-PEG based material containing the indicated concentrations of silk during 4 hours. FIG. 4B shows the swelling profile of the silk-PEG based material during 5 days.

FIG. 5A shows results of in vitro degradation of the samples in 1×PBS (pH 7.4). FIG. 5B shows results of in vitro degradation of the samples in Protease XIV (1 mg/ml, 5 U/mg). n=3. No significant degradation was noticed for any of the indicated conditions.

FIG. 6A illustrates the Dynamic Mechanical Analyses (DMA) measurement experimental set-up and procedures measuring sample adhesion to steel, depicting the steel fixtures from prior to sample mounting to a series of steps during the testing process (from left to right). FIG. 6B shows the bar graphs comparing the adhesive profiles of COSEAL® and silk-PEGs samples containing about 5% silk on intestine substrate (dark bars) and steel substrate (light gray bars). N=3. The insert of FIG. 6B shows DMA setting for adhesion to intestine measurements. The indicated statistics were obtained with Student t test. FIG. 6C shows the bar graphs comparing the adhesive profiles of COSEAL® and silk-PEGs samples containing about 6% silk on intestine substrate (dark bars) and steel substrate (light gray bars).

FIG. 7A shows the results of pH-dependence of adhesion for 10% silk-PEGs biomaterials (n=3) (ANOVA, p=0.009). FIG. 7B shows the results of concentration dependence of adhesion for silk-PEGs biomaterials at pH 6 (n=3)

(ANOVA, p=0.00002. The statistics indicated in the figures were obtained with Student t test. FIG. 7C shows the results of adhesion to steel for 10% silk-PEG biomaterials prepared in water, as compared to that of the PEG-only biomaterial prepared in water and COSEAL®.

FIG. 7D shows the results of adhesion to steel for 10% silk-PEG biomaterials prepared in a phosphate buffered solution, as compared to that of the PEG-only biomaterial prepared in phosphate buffered solution and COSEAL®. FIG. 7E shows the results of adhesion to steel for silk-PEG biomaterials containing various silk concentrations prepared in a phosphate buffered solution, as compared to that of the PEG-only biomaterial prepared in phosphate buffered solution and COSEAL®.

DETAILED DESCRIPTION OF THE INVENTION

Figure 1A:
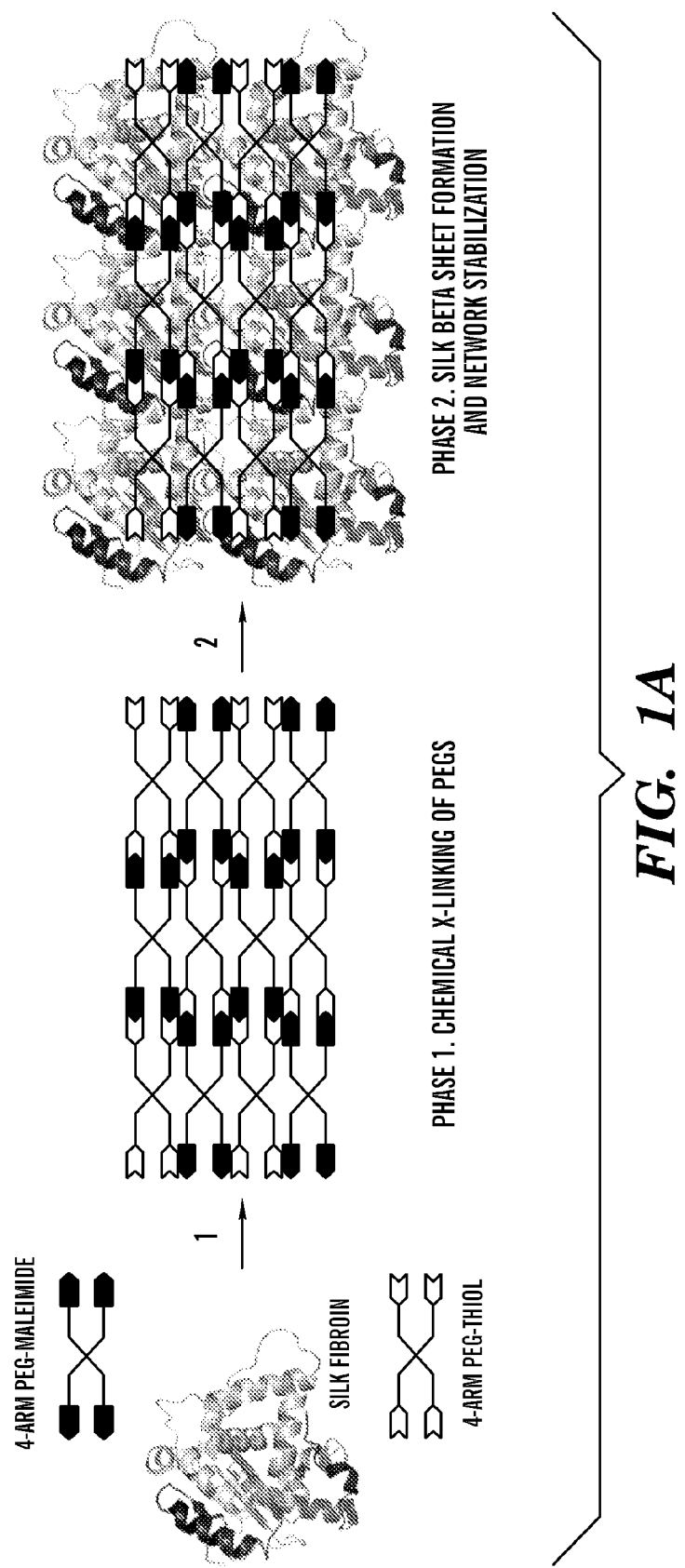
FIGS. 1A-1B show schematic representations of an exemplary formation process of the silk-PEG materials described herein.

The invention relates to methods, compositions, and kits for preparing a silk-containing composite, wherein the silk-containing composite includes silk fibroin and a multi-component gelation system (e.g., two-component gelation system). Examples of two-component gelation systems include, but are not limited to, alginate construct systems, fibrin glues (e.g., fibrinogen and thrombin) and fibrin glue-like systems, self-assembled peptides, synthetic polymer systems (e.g., PEG system) and any combinations thereof. The components of the gelation system (e.g., at least two functionally-activated PEG components) can crosslink with each other rapidly to form a gel, wherein the silk fibroin can stabilize the crosslinked network through silk beta-sheet formation.

In some embodiments, the invention relates to methods, compositions and kits for preparation of silk-PEGs based biomaterials through crosslinking by chemically reacting active polyethylene glycols (PEGs) possessing different chemical groups (e.g., PEGs containing thiol and maleimide functional groups) that are additionally stabilized through the beta-sheet formation of silk. The crosslinked silk-PEGs biomaterials present strong adhesive properties, which are comparable to or better than the current leading PEG-based sealant, depending on the silk concentration in the silk-PEGs materials. In addition, the silk-PEGs based biomaterials are cytocompatible, show decreased swelling behavior, and have longer degradation times, which make them suitable for haemostatic applications where the current available tissue sealant products can be contraindicated.

Matrix-Forming Composition

One aspect of the invention relates to a matrix-forming composition comprising at least three components including silk fibroin and at least two functionally activated PEG components. The silk fibroin can be present in any concentrations within the composition, e.g., ranging from about 5 wt % to about 30 wt %, or from about 10 wt % to about 30 wt %. In one embodiment, the silk fibroin is present at a concentration of at least about 10 wt %. The two functionally activated PEG components can react with one another to form a crosslinked matrix, and the matrix can be additionally stabilized by the beta-sheet formation of the silk fibroin. Typically the two PEG components are not pre-mixed before the formation of the matrix. In some embodiments, each of the PEG component can be blended with silk fibroin (e.g., at a concentration of at least about 10 wt %) before the formation of the matrix.

Functionally Activated PEG Components:

Each of the PEG components is activated with one or more functional groups. The term "activated PEG components" refers to PEG components which have been chemically modified to have two or more functional groups that are capable of chemically reacting with the other functional groups of the same or different PEG component to form covalent bonds, thereby forming a crosslinked matrix. PEGs components herein are typically multifunctionally activated, i.e., containing two or more functional groups (e.g., difunctionally activated, tetrafunctionally activated, or star-branched).

At least one of the PEG components can be a multi-arm PEG derivative (e.g., 2-arm, 4-arm, 8-arm, and 12-arm, etc.). In some embodiments, each of the PEG components can be a multi-arm PEG derivative (e.g., 2-arm, 4-arm, 8-arm, and 12-arm, etc.). The term "multi-arm PEG derivatives" described herein refers to a branched poly(ethylene glycol) with at least about 2, at least about 4, at least about 6, at least about 8, at least about 12 PEG polymer chains or derivatives thereof ("arms") or more. Multi-arm or branched PEG derivatives include, but are not limited to, forked PEG and pendant PEG. An example of a forked PEG can be represented by PEG-YCHZ$_2$, where Y is a linking group and Z is an activated terminal group linked to CH by a chain of atoms of defined length. The International Application No. WO 99/45964, the content of which is incorporated herein by reference in its entirety, discloses various forked PEG structures that can be used for some embodiments of the present invention. The chain of atoms linking the Z functional groups to the branching carbon atom can serve as a tethering group and can comprise, for example, alkyl chains, ether chains, ester chains, amide chains and combinations thereof. A pendant PEG can have functional groups, such as carboxyl, covalently attached along the length of the PEG segment rather than at the end of the PEG chain. The pendant reactive groups can be attached to the PEG segment directly or through a linking moiety, such as alkylene. Additional multi-arm or branched PEG derivatives such as the ones disclosed in the U.S. Pat. No. 5,932,462, the content of which is incorporated herein by reference in their entirety, can be also used for the purpose of the invention. In some embodiments, the multi-arm PEG derivatives can encompass multi-arm PEG block copolymer, e.g., but not limited to, 8-arm (PPO-PEG) block copolymer and 8-arm (PLA-PEG) block copolymer. Methods for producing such multi-arm PEG block copolymer are well known in the art. See, for example, the U.S. Patent Application No.: US 2005/0147681, for exemplary multi-arm PEG block copolymer and methods of making the same.

In the matrix-forming composition described herein, each of the PEG components can have the same or different number of arms. Multi-arms of PEG derivatives, for example, PEG derivatives with at least 4 arms, are typically more efficient for crosslinking reaction. The number of crosslinks or mechanical properties of the crosslinked polymer matrix described herein can be modulated by the number of PEG arms and/or functional groups. In one embodiment, 4-arm PEG derivative is used to form silk-PEG crosslinked matrix. In another embodiment, 8-arm PEG derivative is used to form silk-PEG crosslinked matrix. In some embodiments, The PEG component can also be a combination of PEG derivatives with different arm numbers. Different arms of the PEG component can carry the same or different numbers or types of functional groups.

Various functional groups can be used to activate the PEG component for crosslinking reaction. As described herein, "functional group A" and "functional group B" are generally used to refer to a pair of functional groups capable of chemically reacting with one another and hence are used for activating PEG components for crosslinking reaction. For example, functional group A can be —$NH_2$, thiol (—SH), —$S^-$, —OH, —$PH_2$, —CO—NH—$NH_2$, and any combinations thereof; and functional group B can be —NHS, acrylate, vinyl sulfone, maleimide, —$CO_2N(COCH_2)_2$, —$CO_2H$, —CHO, —$CHOCH_2$, —N=C=O, —$SO_2$CH=$CH_2$, —$N(COCH)_2$, —S—S—($C_5H_4N$), and any combinations thereof. Other functional groups known to the skilled in the art can also be used. In one embodiment, the pair of functional groups in the PEG components is thiol/maleimide. In one embodiment, the pair of functional groups in the PEG components is thiol/acrylate. In another embodiment, the pair of functional groups in the PEG components is amine/N-hydroxysuccinimide. In some embodiments, the pair of PEG components used herein is multi-arm PEG-thiol and multi-arm PEG-maleimide. In one embodiment, the pair of PEG components used herein is 4-arm PEG-thiol and 4-arm PEG-maleimide.

The ratio of different functionally activated PEG components in a matrix-forming composition can depend on the number of functional groups in each PEG component. By way of example only, two functionally activated PEG components can be combined in a ratio ranging from about 10:1 to about 1:10, inclusive, or from about 5:1 to about 1:5, inclusive. In some embodiments, one PEG component can be present in excess after crosslinking reaction. In one embodiment, the two functionally activated PEG components can be combined in a ratio of 1:1. One of skill in the art can determine the ratio of different functionally activated PEG components based on reaction stoichiometry and types of chemical reactions.

The reaction of the functionally activated PEGs in forming a crosslinked network can occur by a number of different chemical reactions depending on the functionality of the groups attached to the PEGs. For example, the gel can be formed by a Michael-type addition reaction or a condensation reaction. In general, a Michael-type addition reaction involves the reaction of an α,β-unsaturated carbonyl with a nucleophile. A Michael-type addition reaction can occur at a pH 6 or greater, e.g., pH 6, pH 7, pH 8, pH 9 or higher. Michael addition reactions are well known by those skilled in the art. Examples of moieties on functionalized PEGs which can undergo a Michael's addition reaction include, but are not limited to: PEG-SH combined with PEG-maleimide; and PEG-SH combined with PEG-acrylate. In some embodiments, the reaction could be activated with a buffer with a pH greater than about 4, by a catalytic amount of various amines or a combination thereof. A condensation reaction is a chemical reaction in which two molecules or moieties react and become covalently bonded to one another by the concurrent loss of a small molecule, often water, methanol, or a type of hydrogen halide such as hydrogen chloride. In polymer chemistry, a series of condensation reactions can take place whereby monomers or monomer chains add to each other to form longer chains. Examples of functional groups on activated PEGs which can undergo a condensation reaction include, but are not limited to, PEG-NHS ester and PEG-$NH_2$. Without wishing to be bound by theory, a Michael addition reaction can contribute to a longer stability of the resulting crosslinked network since thioether bonds are formed as compared to the more hydrolytically labile thioester bonds formed from the reaction of thiols with activated esters.

The PEG component in the matrix-forming composition can be provided as a powder, a suspension or a solution, or one component is provided as a powder and another component is provided as a suspension or a solution. Similarly, silk fibroin in the matrix-forming composition can also be provided as a powder, a suspension or a solution. In one embodiment, all the components in the matrix-forming composition are powders. In one embodiment, at least one component is suspended or dissolved in an aqueous solution. In one embodiment, at least the silk fibroin is provided in an aqueous solution. In one embodiment, the silk fibroin is dissolved or suspended in water to prepare the silk fibroin solution. In another embodiment, the PEG component can be suspended or dissolved in the silk fibroin solution. In some embodiments, the matrix-forming composition is suspended or dissolved in an aqueous solution in the absence of divalent ions, e.g., a buffered solution containing monovalent ions. In one embodiment, the matrix-forming composition is suspended or dissolved in water.

The components of the matrix-forming composition (e.g., PEG components and/or silk fibroin) can be individually prepared and stored in an acidic, neutral or basic solution (i.e., at any pHs). Prior to combining the components into one composition to form a crosslinked polymer matrix, the pH of the components can be each adjusted to a desired pH for crosslinking reaction, e.g., at pH 6 or greater, including pH 7, pH 8, pH 9 or greater. Alternatively, the final pH of the matrix-forming composition can reach pH 6 or higher, including pH 7, pH 8, pH 9 or greater after all the components are combined together. Therefore, at least one component can be prepared in an acidic solution, while the other can be prepared in a basic or neutral solution such that the combination results in a desirable pH, e.g., pH 6, pH 7, pH 8, pH9 or higher.

Without wishing to be bound, it is contemplated that other multi-component gelation systems (e.g., two-component gelation system) can be used to replace PEG gelation system or be included in the matrix-forming composition described herein, provided that silk fibroin can form beta sheet and stabilize the crosslinked network. Examples of two-component gelation systems include, but are not limited to, alginate construct systems, fibrin glues (e.g., fibrinogen and thrombin) and fibrin glue-like systems, self-assembled peptides, synthetic polymer systems (e.g., PEG system) and any combinations thereof.

In some embodiments, the two-component gelation system includes fibrin glue. Fibrin glue consists of two main components, fibrinogen and thrombin. When combined in equal volumes, thrombin converts the fibrinogen to fibrin by enzymatic action at a rate determined by the concentration of thrombin. The result is a biocompatible gel which gelates between about 5 to about 60 seconds. In such embodiments, the silk fibroin can further stabilize the fibrin gel through silk beta-sheet formation. Examples of fibrin glue-like systems include, but are not limited to, Tisseel™ (Baxter), Beriplast P™ (Aventis Behring), Biocol® (LFB, France), Crosseal™ (Omrix Biopharmaceuticals, Ltd.), Hemaseel HMN® (Haemacure Corp.), Bolheal (Kaketsuken Pharma, Japan) and CoStasis® (Angiotech Pharmaceuticals).

In some embodiments, a two-component gelation system is a synthetic polymer system. In addition to PEG as described herein, other examples of synthetic polymers include, but are not limited to, polyamino acids, polysaccharides, polyalkylene oxide and any combinations thereof. In these synthetic polymer systems, at least two components of the synthetic polymer system can be functionally activated using reaction chemistry known in the art such that these two components of the synthetic polymer system can react with each other to form a crosslinked network.

In various embodiments, the molecular weight of each of the PEG components or other synthetic polymers can independently vary depending on the desired application. In some embodiments, the molecular weight (MW) is about 100 Da to about 100000 Da, about 1000 Da to about 20000 Da, or about 5000 Da to about 15000 Da. In some embodiments, the molecular weight of the PEG components is about 10,000 Da.

Silk Fibroin:

As used herein, the term "silk fibroin" includes silkworm fibroin and insect or spider silk protein. See e.g., Lucas et al., 13 Adv. Protein Chem. 107 (1958). Any type of silk fibroin can be used. Silk fibroin produced by silkworms, such as *Bombyx mori*, is the most common and represents an earth-friendly, renewable resource. For instance, silk fibroin can be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that can be used. An aqueous silk fibroin solution can be prepared using techniques known in the art. Suitable processes for preparing silk fibroin solution are disclosed, for example, in U.S. patent application Ser. No. 11/247,358; WO/2005/012606; and WO/2008/127401. See Example 1 for preparation of a silk fibroin solution (~20% w/v), e.g., in deionized water.

The silk fibroin solution can be diluted to a lower concentration with deionized water, or can be concentrated, for example, to about 30% (w/v), if desired. Briefly, the silk fibroin solution with a lower concentration can be dialyzed against a hygroscopic polymer, such as PEG, amylose or sericin, for a time period sufficient to result in a desired concentration. See, e.g., WO 2005/012606.

Additionally, silk fibroin can be chemically modified with active agents in the solution, for example through diazonium or carbodiimide coupling reactions, avidin-biodin interaction, or gene modification and the like, to alter the physical properties and functionalities of the silk protein. See, e.g., PCT/US09/64673; PCT/US10/41615; PCT/US10/42502; U.S. application Ser. No. 12/192,588.

The silk fibroin solution can also be combined with one or more biocompatible polymers such as polyethylene oxide, collagen, fibronectin, keratin, polyaspartic acid, polylysin, alginate, chitosan, chitin, hyaluronic acid, and the like; or one or more active agents, such as cells, enzymes, proteins, nucleic acids, antibodies, antibiotics, hemostatic agents and the like, as described herein. See, e.g., WO2004/062697 and WO2005/012606.

In some embodiments, the silk fibroin solution or matrix-forming composition can further contain porogens, such as salt particles or water-soluble particles to create porous structure in the crosslinked polymer matrix. In such embodiments, the porogens can be removed by leaching the salt particles or water-soluble particles in water or aqueous solution, after the crosslinked polymer matrix has formed. Methods for creating porous structures in silk are known to any one of skill in the art.

The silk aqueous solution can be processed into silk matrix such as silk gels, conformal coatings or layers, mats, sponges, 3-dimentional scaffolds, fibers and other material formats at appropriate conditions.

Methods of Preparing a Crosslinked Polymer Matrix (e.g., Silk-PEG-Based Matrices)

Another aspect of the invention relates to a method of preparing a crosslinked polymer matrix comprising the steps of admixing a matrix-forming composition described herein and crosslinking the components of the composition to form a crosslinked polymer matrix. The composition comprises at least two functionally activated PEG components capable of reacting with one another to form a crosslinked matrix, and silk fibroin capable of forming beta-sheets to further stabilize the crosslinked matrix. The embodiments of the PEG components and silk fibroin of the composition have been described herein.

In some embodiments, silk fibroin used herein can be depleted of sericin by any methods known in the art, e.g., but not limited to, using the method described in Example 1.

When admixing the components of the matrix-forming composition, an aqueous solution (e.g., water or an aqueous solution excluding ions) or solvent (e.g., organic solvents) can be used. In one embodiment, water or deionized water is used to dissolve or suspend, and mix the components of the matrix-forming composition. In some embodiments, a buffered solution can be used to dissolve or suspend, and mix the components of the matrix-forming composition. In such embodiments, a buffer solution can exclude divalent ions, e.g., a buffer solution containing monovalent ions. Alternatively, if one or more components of the composition is provided as a suspension or solution, the other components can be mixed with the suspension or solution with or without the aid of extra solutions or solvents.

A broad percentage range of silk fibroin and PEG components in the composition can be used for preparing the silk-PEGs crosslinked matrix (e.g., wt % or w/v % of silk fibroin and PEG components in the matrix-forming composition). For example, the concentration of silk fibroin in the solution can be less than about 30% (wt % or w/v %) before mixing; and the concentration of each PEG component in the solution can be less than about 30% (wt % or w/v %) before mixing, depending on the solubility and viscosity of PEG solution. Viscosities of silk fibroin solution and PEG solutions can be chosen for ease of administration. In one embodiment, silk fibroin concentrations before mixing can range from about 5% to about 30%, or from about 10% to about 30%, or from about 15% to about 25%. Increasing silk concentration to above 10% can increase the adhesive properties of the resulting silk-PEGs crosslinked matrix. In one embodiment, concentration of each PEG component before mixing ranges from about 1% to about 20%, or from about 5% to about 15%. Increasing concentrations of PEG components can decrease the amount of time needed for crosslinking. The concentration of PEG component can also depend on factors such as molecular weight and nature of functional groups on PEGs. Hence, for example, 8-arm PEG can be present in a smaller weight percentage than the 4-arm counterpart and achieve the same degree of crosslinking in a similar amount of time. An ordinary artisan can optimize the concentrations of silk fibroin or PEG components for various applications, e.g., tissue adhesives or tissue sealants.

Chemical crosslinking between the PEG components can involve rapid gel formation via chemical reaction between the functional groups of the two or more PEG components. This step can occur within seconds upon mixing two PEG components in aqueous solution, and this step of gel formation can occur with either the presence or absence of silk in the PEG components.

Silk fibroins have an unusual amino acid sequence with the bulk of the protein organized into alanine and glycine-rich hydrophobic domains and with the large side chain amino acids clustered in chain-end hydrophilic blocks. Structurally, the hydrophobic blocks are organized into crystalline regions and the hydrophilic blocks form amorphous regions. Zhou et al., 44 Proteins 119-22 (2001). The crystalline regions of silk fibroin have the capacity to organize into crystalline beta-sheets via intra- and intermolecular hydrogen bonding and hydrophobic interactions.

Beta-sheet formation of silk fibroin chains can be induced by various treatments, such as dehydration, mechanical force, or thermodynamic treatment. Dehydrating treatment can refer to drying in the air or in a flow of dehydrating gas such as nitrogen gas, or a dehydrating solvent such as alcohol, e.g., methanol or ethanol, or sodium chloride, or water annealing treatment. See, e.g., WO/2004/062697; WO 2008/127404. Mechanical force includes sheer or elongated force, which can be applied through treatments such as ultrasonication or vortexing. See e.g., U.S. Application Publication No. 2010/0178304; PCT/US2010/036841. Other factors for inducing beta-sheet formation include, but are not limited to, changing temperatures, pHs, and ionic strengths. Wang et al., 36 Intl. J. Biol. Macromol. 66-70 (2005); Kim et al., 5 Biomacromol. 786-92 (2004); Matsumoto et al., 110 J. Phys. Chem. B 21630-38 (2006). Without the described treatments to induce a rapid beta-sheet formation of silk fibroin, the transition of silk fibroin in solution cannot occur or occur very slowly under physiological conditions.

In one embodiment, the crosslinking step involves exposing the mixed components to an alcohol treatment (e.g., methanol or ethanol) or a water-annealing treatment to induce structural transition of silk fibroin from random coil and α-helical rich structures into beta-sheet structures, to further stabilize the crosslinked polymer matrix.

Without being bound by theory, crosslinking of the matrix-forming composition can form a variety of material formats, including gels, mats, films, sponges, 3-dimensional scaffolds, fibers and other material formats.

In one embodiment, the crosslinking of the PEG components and silk fibroin forms a hydrogel (referred to as "silk-PEGs" hydrogel). A "hydrogel" is generally a network of polymer chains that are hydrophilic, sometimes found as a colloidal gel in which water is the dispersion medium. Hydrogels are super-absorbent (they can contain over 99% water) and can be comprised of natural (e.g., silk) or synthetic polymers, e.g., PEG. By way of example only, the silk-PEGs hydrogels can be formed via a two-step process: a covalent, chemical crosslinking between the maleimide and thiol functional groups of four-armed PEG components; and a beta-sheet formation between silk fibroin chains to further stabilize the formed network. The resulting silk-PEGs hydrogels present desired properties for application as tissue sealants: strong adhesive properties, good biocompatibility, side-product free chemistry, rapid crosslinking and slow biodegradability.

To evaluate the properties of the silk-PEGs hydrogels, the hydrogels were characterized in vitro, and the currently commercially available COSEAL® product was chosen as a reference to evaluate the performance of the silk-PEGs gels. See Examples 1-7; FIGS. 1A-8B.

COSEAL® is Food and Drug Administration (FDA)-approved and is composed of a thiol-PEG component and a succinimide-PEG component, a dilute hydrogen chloride solution and a sodium phosphate/sodium carbonate solution. The COSEAL® product is available as a kit containing a two-component (e.g., liquid and powder), epoxy-like syringe that upon mixing, the components crosslink within 5-10 seconds to achieve hemostasis. In clinical trials, COSEAL® was well tolerated by patients and its use leads to sealing of oozing wounds in 50% of patients compared to 26% that are treated by standard treatments. For brisk bleeding, COSEAL® was effective in 41% of cases compared to 3% treated with standard treatments. However, this product has certain drawbacks, such as its cumbersome preparation/reconstitution prior to use and its large swelling ratio. For example, reconstitution of COSEAL® requires its PEG components, supplied as a powder, to be mixed back and forth between two syringes at least 20 times until the components are completely dissolved. Additionally, COSEAL® product swells to about 400% of its original size/weight, hence limiting its applicability to areas where nerve compression would not be an issue. (COSEAL® package insert)

Without being bound by theory, it is believed that the adhesive properties of silk-PEGs hydrogels are comparable to or even better than COSEAL®. The in vitro adhesion characterization was conducted on steel substrate after confirming that the adhesion trends on this substrate correlate well with those observed on biological membranes (bovine intestines). Silk-PEGs samples containing 10%-15% w/v silk fibroin, showed comparable adhesion values to the COSEAL® control; while the silk-PEGs samples containing 20% w/v silk fibroin showed at least about 50% increase in adhesiveness compared to the COSEAL® control. See Examples 1 and 6; and FIGS. 6A-7E. In some embodiments, increasing the concentration of the silk fibroin solution to a concentration of at least about 10 wt %, at least about 15 wt %, at least about 20 wt % or higher, can increase an adhesion strength of the resultant crosslinked polymer matrix to at least about 10 Pa, at least about 15 Pa, at least about 20 Pa, at least about 30 Pa, at least about 40 Pa, at least about 50 Pa, at least about 60 Pa, at least about 70 Pa, at least about 80 Pa, at least about 90 Pa, at least about 100 Pa, or higher.

Silk concentrations in the silk-PEGs-based biomaterial can range from 3 wt % to 50 wt %, from about 10 wt % to about 40 wt %, from about 15 wt % to about 40 wt %, from about 20 wt % to about 30 wt %. Decreasing silk concentrations typically yields solutions with lower viscosities and requires fewer raw materials; however, the adhesive properties of the silk-PEGs materials are generally better at silk concentrations at about 10% or higher. At these silk concentrations, the viscosities of silk solution can still be suitable for injection.

The pH for silk and PEGs solutions when preparing the silk-PEGs material can present a broad range (e.g., 1-15). To make the silk-PEGs materials suitable for biomedical uses, the pH is typically within the physiological range (e.g., 6-8). Without being bound by theory, the silk-PEGs materials prepared at pH neutral or slightly acidic (e.g., pH=6) can present better adhesive properties. See, for instance, Example 6 and FIG. 7A.

Moreover, the silk-PEGs hydrogels can overcome some of the drawbacks associated with COSEAL®, such as significant swelling and short in vivo residence time. The swelling ratio of silk-PEGs sealants is between 60-70%, while COSEAL® increases its size to up to 400% upon application. See Examples 1 and 4, and FIGS. 4A and 4B. This property of the silk-PEGs hydrogels can increase the application spectra of silk-PEGs as sealants and allow them to be used in close spaces or in the vicinity of pressure-sensitive structures such as nerves, where the use of COSEAL® is contraindicated.

The silk-PEGs hydrogel is stabilized at least partially by the chemical crosslinking between PEG components, which is comparable to COSEAL®, and additionally consolidated over time via the secondary physical crosslinking reaction involving the beta-sheet formation of silk fibroin. This provides an attractive feature in the use as a tissue sealant—the long in vivo residence time. COSEAL® is degraded in approximately 1-2 weeks (Wallace et al., 2001) while the silk-PEGs based materials can be present for a significantly longer time (Horan et al., 2005), allowing for complete healing, or more complete healing, prior to the materials being fully resorbed. See, also, Examples 1 and 5, and FIGS. 5A and 5B.

In contrast to COSEAL®, which is based on chemical crosslinking of PEG components only, silk-PEGs based materials present dual nature (i.e., incorporating two types of macromolecules: PEG components and silk fibroins) and are formed through a two-step crosslinking mechanism, which offer a series of advantages and allow for a wide spectrum of applications. For example, the versatile properties and material formats of silk fibroin confer various functionalities to the silk-PEGs based materials. Since silk fibroin can be processed to different materials format, silk-PEGs can also be processed to gels, mats, sponges, fibers and other material formats by techniques known in the art. See Altman et al., 23 Biomaterials 4131-41 (2002); Kim et al., 5 Biomacromolecules 786-92 (2004); Li et al., 27 Biomaterials 3115-24 (2006); Nazarov et al., 5 Biomacromolecules 718-26 (2004). All of which are herein incorporated by reference in their entirety. Moreover, the cytocompatibility results for the silk-PEGs based materials indicate that the silk-PEGs based materials do not promote cell spreading, making the materials suitable as a component in anti-scar formation systems. See, for instance, Examples 1 and 3; and FIG. 3. This feature, combined with their versatile processability can also expand the application spectrum of these materials (e.g., allow for production of anti-adhesive sheets or films). Likewise, the silk-PEG based materials are suitable as hemostatic materials to control bleeding.

Crosslinked Polymer Matrix of the Invention (e.g., Silk-PEG-Based Matrices)

Another aspect of the invention relates to a crosslinked polymer matrix formed from mixing the matrix-forming composition. The crosslinked polymer matrix comprises silk fibroin (e.g., at a concentration of at least about 10 wt %) and at least two functionally activated PEG components that have reacted with one another to form a crosslinked matrix, the silk fibroin having formed beta-sheets to stabilize the crosslinked matrix.

In one embodiment, the silk-PEGs biomaterial can contain at least one active agent. To form these materials, the silk fibroin or PEGs components can be mixed with an active agent prior to forming the matrix, or the active agent can be loaded into the silk-PEGs biomaterial after it is formed.

The active agent can represent any material capable of being embedded in the silk-PEGs biomaterials. For example, the active agent can be a therapeutic agent, or a biological material, such as cells (including stem cells), proteins, peptides, nucleic acids (e.g., DNA, RNA, siRNA), nucleic acid analogs, nucleotides, oligonucleotides, peptide nucleic acids (PNA), aptamers, antibodies or fragments or portions thereof (e.g., paratopes or complementarity-determining regions), antibody-like molecules, antigens or epitopes, hormones, hormone antagonists, growth factors or recombinant growth factors and fragments and variants thereof, cell attachment mediators (such as RGD), cytokines, enzymes, small molecules, drugs, dyes, amino acids, vitamins, antioxidants, antibiotics or antimicrobial compounds, anti-inflammation agents, antifungals, viruses, antivirals, toxins, prodrugs, chemotherapeutic agents, hemostatic agents, or combinations thereof. See, e.g., PCT/US09/44117; U.S. Patent Application Ser. No. 61/224,618). The active agent can also be a combination of any of the above-mentioned agents. Encapsulating either a therapeutic agent or biological material, or the combination of them, is desirous because the encapsulated product can be used for numerous biomedical purposes.

In some embodiments, the active agent can also be an organism such as a fungus, plant, animal, bacterium, or a virus (including bacteriophage). Moreover, the active agent can include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents can also include therapeutic compounds, such as pharmacological materials, vitamins, sedatives, hypnotics, prostaglandins and radiopharmaceuticals.

Exemplary cells suitable for use herein can include, but are not limited to, progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above. See also WO 2008/106485; PCT/US2009/059547; WO 2007/103442.

Exemplary antibodies that can be incorporated in silk fibroin include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab. The active agents can also be the combinations of any of the antibodies listed above.

Exemplary antibiotic agents include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents can also be antimicrobial peptides such as defensins, magainin and nisin; or lytic bacteriophage. The antibiotic agents can also be the combinations of any of the agents listed above. See also PCT/US2010/026190.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like. Interactions between components can also be used to functionalize silk fibroin through, for example, specific interaction between avidin and biotin. The active agents can also be the combinations of any of the enzymes listed above. See e.g., PCT/US2010/042585.

When introducing therapeutic agents or biological material into the silk-PEGs biomaterial, other materials known in the art can also be added with the agent. For instance, it can be desirable to add materials to promote the growth of the active agent (for biological materials), promote the functionality of the agent after it is released from the silk-PEGs biomaterial, or increase the agent's ability to survive or retain its efficacy during the period it is embedded in the silk-PEGs biomaterial. Materials known to promote cell growth include cell growth media, such as Dulbecco's Modified Eagle Medium (DMEM), fetal bovine serum (FBS), non-essential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF-I), bone morphogenetic growth factors (BMPs), nerve growth factors, and related proteins can be used. Growth factors are known in the art, see, e.g., Rosen & Thies, CELLULAR & MOLECULAR BASIS BONE FORMATION & REPAIR (R.G. Landes Co., Austin, Tex., 1995). Additional options for delivery via the silk-PEGs biomaterial include DNA, siRNA, antisense, plasmids, liposomes and related systems for delivery of genetic materials; peptides and proteins to activate cellular signaling cascades; peptides and proteins to promote mineralization or related events from cells; adhesion peptides and proteins to improve silk-PEGs-tissue interfaces; antimicrobial peptides; and proteins and related compounds.

Additional biocompatible material can also be blended into the silk-PEGs biomaterial, such as collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, glycerol (see PCT/US2009/060135), and other biocompatible polymers, see WO 2004/0000915. Alternatively, the silk can be mixed with hydroxyapatite particles, see PCT/US08/82487. As noted herein, the silk fibroin can be of recombinant origin, which provides for further modification of the silk such as the inclusion of a fusion polypeptide comprising a fibrous protein domain and a mineralization domain, which are used to form an organic-inorganic composite. These organic-inorganic composites can be constructed from the nano- to the macro-scale depending on the size of the fibrous protein fusion domain used, see WO 2006/076711. See also U.S. patent application Ser. No. 12/192,588.

The silk-PEGs biomaterial, when embedded with active agents or biological materials, can be suitable for long term storage and stabilization of the active agents. Cells and/or active agents, when incorporated in the silk-PEGs biomaterial, can be stable (i.e., maintaining at least 50% of residual activity) for at least 30 days at room temperature (i.e., 22° C. to 25° C.) and body temperature (37° C.). Hence, temperature-sensitive active agents, such as some antibiotics or hemostatic agents, can be stored in silk-PEGs biomaterial without refrigeration. Importantly, temperature-sensitive bioactive agents can be delivered (e.g., through injection) into the body through the silk-PEGs biomaterial and maintain activity for a longer period of time than previously imagined. See, e.g., PCT/US2010/026190.

The silk-PEGs biomaterial with embedded active agents (e.g., therapeutic agents) can be suitable for biodelivery. Techniques for using silk fibroin as a biodelivery device can be found, for example, in U.S. patent application Ser. No. 10/541,182; Ser. No. 11/628,930; Ser. No. 11/664,234; Ser. No. 11/407,373; PCT/US07/020,789; PCT/US08/55072; PCT/US09/44117. Some embodiments of the present invention relate to the utility of silk-PEGs biomaterial with embedded therapeutic agents or biological materials as drug delivery systems for potential utility in medical implants, tissue sealants and tissue repairs.

The structure of silk-PEGs crosslinked matrix enables a controlled release of the delivery of the embedded active agents (e.g., therapeutic agents or biological materials). Controlled release permits dosages to be administered over time, with controlled release kinetics. In some instances, delivery of the therapeutic agent or biological material is continuous to the site where treatment is needed, for example, over several weeks. Controlled release over time, for example, over several days or weeks, or longer, permits continuous delivery of the therapeutic agent or biological material to obtain preferred treatments. The controlled delivery vehicle is advantageous because it protects the therapeutic agent or biological material from degradation in vivo in body fluids and tissue, for example, by proteases. See, e.g., PCT/US09/44117.

Controlled release of the bioactive agent from the silk-PEGs crosslinked matrix can be designed to occur over time, for example, for greater than about 12 hours or 24 hours, inclusive; greater than 1 month or 2 months or 5 months, inclusive. The time of release can be selected, for example, to occur over a time period of about 12 hours to 24 hours, or about 12 hours to 1 week. In another embodiment, release can occur for example on the order of about 1 month to 2 months, inclusive. The controlled release time can be selected based on the condition treated. For example, a particular release profile can be more effective where consistent release and high local dosage are desired.

A pharmaceutical formulation can be prepared that contains the silk-PEGs hydrogel having encapsulated bioactive agents (e.g., therapeutic agent). The formulation can be administered to a patient in need of the particular active agent that has been encapsulated in the silk-PEGs hydrogels. The pharmaceutical formulation can be administered by a variety of routes known in the art including topical, oral, ocular, nasal, transdermal or parenteral (including intravenous, intraperitoneal, intramuscular and subcutaneous injection as well as intranasal or inhalation administration), and implantation. The delivery can be systemic, regional, or local. Additionally, the delivery can be intrathecal, e.g., for delivery to the central nervous system.

The amount of therapeutic agent will depend on the particular drug being employed and medical condition being treated. For example, the amount of drug can represent about 0.001% to about 70%, or about 0.001% to about 50%, or about 0.001% to about 20% by weight of the material. Upon contact with body fluids or body tissues, the drug will be released.

When desired, the active agent-containing silk-PEGs hydrogel can include a targeting ligand or precursor targeting ligand. Targeting ligand refers to any material or substance which can promote targeting of the pharmaceutical formulation to tissues and/or receptors in vivo and/or in vitro. The targeting ligand can be synthetic, semi-synthetic, or naturally-occurring. Materials or substances which can serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs, peptide nucleic acids (PNA), aptamers, and polynucleotides. Other targeting ligands in the present invention include cell adhesion molecules (CAM), among which are, for example, cytokines, integrins, cadherins, immunoglobulins and selectin. A precursor to a targeting ligand refers to any material or substance which can be converted to a targeting ligand. Such conversion can involve, for example, anchoring a precursor to a targeting ligand. Exemplary targeting precursor moieties include maleimide groups, disulfide groups, such as ortho-pyridyl disulfide, vinylsulfone groups, azide groups, and iodo acetyl groups.

In preparation for in vivo application, formulations containing the silk-PEGs hydrogels can be formulated to include excipients. Exemplary excipients include diluents, solvents, buffers, or other liquid vehicle, solubilizers, dispersing or suspending agents, isotonic agents, viscosity controlling agents, binders, lubricants, surfactants, preservatives, stabilizers and the like, as suited to particular dosage form desired. The formulations can also include bulking agents, chelating agents, and antioxidants. Where parenteral formulations are used, the formulation can additionally or alternately include sugars, amino acids, or electrolytes.

More specifically, examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; oils such as peanut oil, cottonseed oil; safflower oil, sesame oil; olive oil; corn oil and soybean oil; esters such as ethyl oleate and ethyl laurate; agar; non-toxic compatible lubricants such as sodium lauryl sulfate and magnesium stearate; polyols, for example, of a molecular weight less than about 70,000 kD, such as trehalose, mannitol, and polyethylene glycol. See, e.g., U.S. Pat. No. 5,589,167. Exemplary surfactants include nonionic surfactants, such as Tween surfactants, polysorbates, such as polysorbate 20 or 80, etc., and the poloxamers, such as poloxamer 184 or 188, pluronic polyols, and other ethylene/polypropylene block polymers, etc. Suitable buffers include Tris, citrate, succinate, acetate, or histidine buffers. Suitable preservatives include phenol, benzyl alcohol, metacresol, methyl paraben, propyl paraben, benzalconium chloride, and benzethonium chloride. Other additives include carboxymethylcellulose, dextran, and gelatin. Suitable stabilizing agents include heparin, pentosan polysulfate and other heparinoids, and divalent cations such as magnesium and zinc. Coloring agents, releasing agents, coating agents, sweetening, flavoring and perfuming agents, preservatives and antioxidants can also be present in the composition, according to the judgment of the formulator or ordinary skill.

In various embodiments, the crosslinked polymer matrix described herein can swell under specified conditions. For example, when exposed to a physiological condition, the crosslinked polymer can swell less than 90 wt %, 80 wt %, less than 70 wt %, less than 60 wt %, less than 50 wt %, less than 40 wt % of the initial weight or size of the crosslinked polymer matrix or lower. As used herein, the term "physiological condition" refers to temperature, pH, ionic strength, viscosity, and/or other biochemical parameters which typically exist in vivo in a viable subject or organism (e.g., a mammalian subject). The phase "initial weight or size of the crosslinked polymer matrix" as used herein can refer to the weight or size (e.g., volume) of the crosslinked polymer matrix in a solid state (including gel state) prior to exposure to a physiological condition. In some embodiments, the phase "initial weight or size of the crosslinked polymer matrix" as used herein can refer to the weight or size (e.g., volume) of the respective matrix-forming composition. The swelling ratio of such crosslinked polymer matrices described herein is significantly smaller than the FDA-approved tissue sealant COSEAL® (which swells ~400% of its original size/weight upon administration to a subject). Thus, the crosslinked polymer matrix described herein can be a better biomaterial than COSEAL® when used in tissue or organ areas in the vicinity of pressure sensitive areas, e.g., in the vicinity of nerves, where nerve compression would be an issue.

In some embodiments, the crosslinked polymer matrix can retain its volume under specified conditions. For example, when placed in vivo, the crosslinked polymer matrix can retain at least about 30%, at least about 40%, at least about 50%, at least about 60%, at least about 70%, at least about 80%, at least about 90%, at least about 90% of its original volume for a period of time. The term "original volume" as used herein can refer to the volume or size of the crosslinked polymer matrix prior to placement in vivo. In some embodiments, the term "original volume" as used herein can refer to the administration volume of the crosslinked polymer matrix to a subject. In various embodiments, the crosslinked polymer matrix can retain at least a portion of its original volume for at least about 5 days, at least about 10 days, at least about 15 days, at least 20 days, at least about 1 month, at least about 2 months, at least about 3 months, at least about 4 months, at least about 5 months, at least about 6 months, at least about 1 year, at least about 2 years or longer. In some embodiments, the crosslinked polymer matrix can retain at least a portion of its original volume until wound healing is complete, for example, sides or edges of the wound are rejoined to form a continuous barrier (e.g., intact skin).

In some embodiments, the crosslinked polymer matrix described herein can possess adhesive capabilities. Depending upon desired applications, the adhesion strength of the crosslinked polymer matrices can be modulated by various factors, e.g., but not limited to, concentration of silk fibroin, pH values and/or solvent used for preparing the crosslinked polymer matrix. In some embodiments, the crosslinked polymer matrix can be adapted to have an adhesion strength of at least about 5 Pa, at least about 10 Pa, at least about 15 Pa, at least about 20 Pa, at least about 30 Pa, at least about 40 Pa, at least about 50 Pa, at least about 60 Pa, at least about 70 Pa, at least about 80 Pa, at least about 90 Pa, at least about 100 Pa or higher. In some embodiments, the crosslinked polymer matrix can be adapted to have an adhesion strength comparable to that of COSEAL®, e.g., at least about 10 Pa. The term "adhesion strength" as used herein generally refers to the pull-force strength to break the contact between a crosslinked polymer matrix and a substrate on which the crosslinked polymer matrix was applied. In some embodiments, the substrate can be a surface of at least a part of a tissue or an organ. In some embodiments, the substrate can be a surface of an implant. In another embodiment, the substrate can be a metal (e.g., a steel surface) or plastic surface. Methods for measuring adhesion strength of different materials are well known in the art. An exemplary method for measuring adhesion strength is also included in Example 1.

Applications of the Crosslinked Polymer Matrix Described Herein

The silk-PEGs hydrogels present desirable properties for application as tissue sealants or adhesives: strong adhesive properties, good biocompatibility, side-product free chemistry, rapid crosslinking and slow biodegradability.

Accordingly, the silk-PEGs hydrogels can be used in a method of forming a tissue sealant or adhesive on a target site of a subject, e.g., an open wound of a subject. The method comprises administering to a target site (e.g., an open wound) of a subject at least a composition comprising at least two functionally activated PEG components capable of reacting with one another to form a crosslinked matrix, and a silk fibroin capable of forming beta-sheets to stabilize the crosslinked matrix; and mixing the components of the composition to crosslink the components and form a tissue sealant or adhesive on the target site (e.g., wound).

In one embodiment, the two PEG components are separately administered to the wounded site of the subject thereby forming the tissue sealant in vivo. The silk-PEGs based tissue sealant can be formed upon application to the wound, which can be a tissue or an organ. In such embodiments, the crosslinked polymer matrix or tissue sealants are formed in situ. In other embodiments, the crosslinked polymer matrix can be formed prior to placement into a subject, e.g., by implantation.

The silk-PEGs based tissue sealant can also be formed on an implant, or to cros slink the implant with the surrounding tissues or organs. When forming a tissue sealant on a subject, the surface of the wounded site can be crosslinked with at least one of the components.

In some embodiments, at least one active agent described herein can be delivered prior to, concurrently with, or after administering PEG components and/or silk fibroin to a target site of a subject. In some embodiments, the active agent can be mixed with at least one of the components of the matrix-forming composition described herein. In some embodiments, the active agent can be delivered separately from the components of the matrix-forming composition described herein.

Wounds to be treated include open or closed, or as either acute or chronic in origin. In one embodiment, the silk-PEGs based tissue sealant is used to treat an open wound. Open wounds include, but are not limited to, incisions or incised wounds; lacerations or irregular tear-like wounds caused by some blunt trauma; avulsion; abrasions (grazes) such as superficial wounds in which the topmost layer of the skin (the epidermis) is scraped off; puncture wounds such as those caused by an object puncturing the skin; penetration wounds such as those caused by an object entering and coming out from the skin; and gunshot wounds. The wounds to be treated here can also include closed wounds such as contusions, hematomas, crush injury, chronic or acute wounds.

The silk-PEGs based tissue sealant formed at the wound site can further contain hemostatic agents since hemostatic agents typically act to stop bleeding and tissue sealant can bind to and close defects in the tissues. Combining the hemostatic agents into the silk-PEGs based tissue sealant can therefore present desirable features during surgical repair to prevent or stop bleeding as well as promote tissue reconstruction. Exemplary hemostatic agents suitable for use herein include, but are not limited to, thrombin, fibrin, fibrinogen, gelatin, collagen, polysaccharide, cellulose, blood factors, and combinations thereof.

The silk-PEGs based tissue sealant can overcome some of the drawbacks associated with commercially available tissue sealants such as significant swelling. As described herein, the swelling ratio of silk-PEGs sealants is significantly decreased compared to, for instance, COSEAL®. The silk-PEGs hydrogels therefore can be used in close spaces or in the vicinity of pressure-sensitive structures such as nerves.

In some embodiments, the crosslinked polymer matrix (e.g., silk-PEG-based matrices) can be used for cell or drug delivery, or as a platform for cells to grow.

The invention also provides kits and device containing the matrix-forming composition and instructions to carry out any of the methods described herein. The matrix-forming composition as described herein comprises at least three components including silk fibroin and at least two functionally activated PEG components. The embodiments of silk fibroin and PEG components of the composition are described herein.

The kits can also contain one or more active agents such as hemostatic agents. The kits can comprise one or more containers or mixing tools (e.g., a vial, ampoule, syringes, or other suitable storage container). Silk fibroin, PEGs components, active agents, or reagents that can be needed for crosslinking can be enclosed in the containers or mixing tools with each component enclosed separately or as a mixture (e.g., PEG can be suspended or dissolved in silk fibroin solution).

In some embodiments, the matrix-forming compositions can be pre-loaded into a delivery device, e.g., a double-barreled injection device. In such embodiments, by way of example only, one PEG component mixed with silk fibroin can be pre-loaded in one barrel of the delivery device, while another PEG component optionally mixed with silk fibroin can be pre-loaded in another barrel of the delivery device. The components inside the barrels can be present in powder, which will be suspended into a solution at time of use, or they can be pre-suspended in a solution. In other embodiments, the components of the matrix-forming compositions can be pre-loaded into separate delivery devices, e.g., syringes.

The instructions in the kit relating to the use of the kit for carrying out the invention generally describe how the contents of the kit are used to carry out the methods of the invention. Instructions can include sample information (e.g., forms, sizes), steps and conditions necessary to form silk-PEGs crosslinked matrix, and the like. Instructions supplied in the kits can include written instructions on a label or package insert (e.g., a paper sheet included in the kit), or machine-readable instructions (e.g., instructions carried on a magnetic or optical storage disk).

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials can be used in the practice or testing of the invention, the methods, devices, and materials in this regard are described herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The present invention can be defined in any of the following numbered paragraphs:

1. A method of preparing a crosslinked polymer matrix, comprising:
    admixing a composition comprising
    at least two functionally activated PEG components capable of reacting with one another to form a crosslinked matrix, and
    silk fibroin at a concentration of at least about 10 wt % capable of forming beta-sheets to further stabilize the crosslinked matrix.
2. A method of preparing a crosslinked polymer matrix, comprising:
    admixing a composition comprising
    at least two functionally activated PEG components capable of reacting with one another to form a crosslinked matrix, and
    silk fibroin at a concentration of at least about 10 wt % capable of forming beta-sheets to further stabilize the crosslinked matrix; and
    crosslinking the components of the composition to form a crosslinked polymer matrix.
3. The method of paragraph 2, wherein the cros slinking step involves exposing the mixture to an alcohol treatment or a water-annealing treatment.
4. The method of any of paragraphs 1-3, wherein the silk fibroin is depleted of sericin before admixing with the functionally activated PEG components.
5. The method of any of paragraphs 1-4, wherein the matrix is a hydrogel.
6. The method of any of paragraphs 1-5, wherein each PEG component is a four-armed PEG.
7. The method of any of paragraphs 1-6, wherein one of the PEG components is functionally activated with a maleimidyl group.
8. The method of any of paragraphs 1-7, wherein one of the PEG components is functionally activated with a thiol group.
9. The method of any of paragraphs 1-8, wherein one of the PEG components is functionally activated with a maleimidyl group and another one of the PEG components is functionally activated with a thiol group.
10. The method of any of paragraphs 1-9, wherein at least one component of the composition is suspended or dissolved in an aqueous solution.
11. The method of paragraph 10, wherein at least the silk fibroin is in the aqueous solution, and the silk fibroin concentration is at least about 10 wt %.
12. The method of paragraph 10 or 11, wherein the aqueous solution excludes divalent ions.
13. The method of paragraph 12, wherein the aqueous solution is deionized water.
14. The method of any of paragraphs 1-13, wherein each PEG component is suspended or dissolved in the silk fibroin solution at a concentration of at least about 10 wt %.
15. The method of any of paragraphs 1-14, wherein the pH of the aqueous solution ranges from about 6 to about 8.
16. The method of any of paragraphs 1-15, wherein the concentration of each PEG component in the composition ranges from about 2.5 wt % to about 15 wt %.
17. The method of any of paragraphs 1-16, wherein the concentration of the silk fibroin in the composition ranges from about 10 wt % to about 30 wt %.
18. The method of any of paragraphs 1-17, wherein the concentration of the silk fibroin in the composition ranges from about 15 wt % to about 25 wt %.
19. The method of any of paragraphs 1-18, wherein the crosslinked polymer matrix swells less than about 70% of the initial weight of the composition.
20. The method of paragraph 19, wherein the crosslinked polymer matrix does not substantially swell within one hour after the admixing step.
21. The method of any of paragraphs 1-20, wherein the silk fibroin at a concentration of at least about 10 wt % increases an adhesive strength of the crosslinked polymer matrix to at least about 10 Pa.
22. The method of any of paragraphs 1-21, wherein the composition further comprises an active agent selected from the group consisting of cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, and any combinations thereof.
23. The method of paragraph 22, wherein the active agent is a cell selected from the group consisting of progenitor cells or stem cells, smooth muscle cells, skeletal muscle cells, cardiac muscle cells, epithelial cells, endothelial cells, urothelial cells, neurons, germ cells, connective tissue cells, hormone-secreting cells, tenocytes, fibroblasts, myoblasts, neuroblasts, glioblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, precursor cells, and any combinations thereof.

24. The method of paragraph 22, wherein the active agent is an antibiotic.

25. The method of any of paragraphs 1-24, wherein the composition further comprises a hemostatic agent selected from the group consisting of thrombin, fibrin, fibrinogen, gelatin, collagen, polysaccharide, cellulose, blood factors, and any combinations thereof.

26. The method of any of paragraphs 1-25, wherein the crosslinked polymer matrix retains its original volume in a physiological condition for at least 10 days.

27. A crosslinked polymer matrix produced by the method of any of paragraphs 1-26.

28. A tissue sealant or adhesive comprising the crosslinked polymer matrix of paragraph 27.

29. A method of forming a tissue sealant or adhesive on a target site of a subject, comprising:
   administering to the target site of the subject a composition comprising
      at least two functionally activated PEG components capable of reacting with one another to form a crosslinked matrix, and
      a silk fibroin at a concentration of at least about 10 wt % capable of forming beta-sheets to stabilize the crosslinked matrix; and
   mixing the components of the composition to cros slink the components and form a tissue sealant or an adhesive on the target site.

30. The method of paragraph 29, wherein each PEG component is a four-armed PEG.

31. The method of paragraph 29 or 30, wherein one of the PEG components is functionally activated with a maleimidyl group.

32. The method of any of paragraphs 29-31, wherein one of the PEG components is functionally activated with a thiol group.

33. The method of any of paragraphs 29-32, wherein one of the PEG components is functionally activated with a maleimidyl group and another one of the PEG components is functionally activated with a thiol group.

34. The method of any of paragraphs 29-33, wherein at least one component is suspended or dissolved in an aqueous solution.

35. The method of paragraph 34, wherein at least the silk fibroin at a concentration of at least about 10 wt % is in the aqueous solution.

36. The method of paragraph 35, wherein the aqueous solution excludes divalent ions.

37. The method of any of paragraphs 29-36, wherein each PEG component is suspended or dissolved in the silk fibroin solution at a concentration of at least about 10 wt %.

38. The method of any of paragraphs 29-37, wherein the weight percentage of each PEG component based on total weight of the composition ranges from about 2.5 wt % to about 15 wt %.

39. The method of any of paragraphs 29-38, wherein the weight percentage of the silk fibroin based on total weight of the composition ranges from about 10 wt % to about 30 wt %.

40. The method of any of paragraphs 29-39, wherein the weight percentage of the silk fibroin based on total weight of the composition ranges from about 15 wt % to about 25 wt %.

41. The method of any of paragraphs 29-40, wherein the tissue sealant or adhesive swells less than about 70 wt % of the initial weight of the composition.

42. The method of any of paragraphs 29-41, wherein the composition further comprises an active agent.

43. The method of any of paragraphs 29-42, wherein the composition further comprises a hemostatic agent.

44. The method of any of paragraphs 29-43, wherein a surface of the target site is crosslinked with at least one of the components in the composition.

45. The method of any of paragraphs 29-44, wherein the subject is an implant.

46. The method of any of paragraphs 29-45, wherein the subject is a tissue or organ.

47. The method of paragraph 46, wherein the tissue or organ is in the vicinity of pressure sensitive structures.

48. The method of paragraph 46 or 47, wherein the tissue or organ has an open wound.

49. The method of any of paragraphs 29-48, wherein the two PEG components are separately administered to the subject thereby forming the tissue sealant or adhesive in vivo.

50. A pre-loaded delivery device comprising
   a housing containing at least two compartments, wherein a first compartment contains a first functionally activated PEG component and a second compartment contains a second functionally activated PEG component capable of reacting with the first functionally activated PEG component to form a crosslinked matrix, and wherein at least one of the first and the second compartments further comprises silk fibroin at a concentration of at least about 10 wt % capable of forming beta-sheets to further stabilize the crosslinked matrix.

51. The delivery device of paragraph 50, wherein the first functionally activated PEG component comprises at least one maleimidyl group.

52. The delivery device of paragraph 50, wherein the second functionally activated PEG component comprises at least one thiol group.

53. The delivery device of any of paragraphs 50-52, wherein the delivery device is a syringe.

54. The delivery device of paragraph 53, wherein the syringe further comprises a needle.

55. The delivery device of paragraph 53 or 54, wherein the syringe further comprises a catheter.

56. A kit comprising:
   a matrix-forming composition containing at least three components pre-loaded into at least one delivery device, wherein the at least three components comprise at least two functionally activated PEG components capable of reacting with one another to form a crosslinked matrix, and silk fibroin at a concentration of at least about 10 wt % capable of forming beta-sheets to further stabilize the crosslinked matrix; and
   at least one container containing a solvent for mixing the matrix-forming composition.

57. The kit of paragraph 56, wherein the delivery device contains at least two separate barrels, wherein each barrel is loaded with a different component of the matrix composition.

58. The kit of paragraph 56, wherein at least one component is pre-loaded into a separate delivery device.
59. The kit of any of paragraphs 56-58, wherein the solvent is an aqueous solution.
60. The kit of any of paragraphs 56-59, wherein the solvent is deionized water.
61. The kit of any of paragraphs 56-60, wherein the PEG components are separately pre-loaded into separate barrels of the delivery device or into different delivery devices.
62. The kit of any of paragraphs 56-61, wherein the PEG components are blended with the silk fibroin.

EXAMPLES

Example 1

Exemplary Materials and Methods

Materials:

The four-arm polyethylene glycol maleimide (4-arm PEG-maleimide) and four-arm polyethylene glycol thiol (4-arm PEG-SH) were purchased from Nanocs Inc., New York, N.Y. Silk worm cocoons were obtained from School of Materials Engineering, Soochow University, Suzhou, China.

Preparation of Silk Fibroin Solution:

Silk fibroin aqueous solution was obtained as previously described. See Sofia et al., 54 J. Biomed. Mater. Res. 139-48 (2001). Briefly, *Bombyx mori* cocoons were cleaned and cut into small pieces. In a subsequent degumming process, sericin, a water-soluble glycoprotein bound to raw silk fibroin filaments, was removed from the silk strands by boiling *Bombyx mori* cocoons in a 0.2 M aqueous solution of $Na_2CO_3$ for 30 minutes to 60 minutes. The silk fibroin was then dissolved in a 9 M LiBr solution at 60° C. for 1 hr to generate a 20% (w/v) silk fibroin solution. The solution was dialyzed in Slide-A-Lyzer® 3500 MWCO dialysis cassettes (Pierce Chemicals, Rockford, Ill.) against water for 72 hr to remove the LiBr.

Gel Formation and Beta-Sheet Content Determination:

Silk-PEGs based hydrogels were prepared using formulations shown in Table 1 or 2, with 1×PBS at pH 6-8 as a solvent (this range was assessed based on the pH specificity of the crosslinking reaction). In some embodiments, the PBS used herein does not contain divalent ions, such as calcium ions. For example, for preparation of a control sample containing PEG components only, 4-arm PEG-SH and 4-arm PEG-maleimide were each dissolved in 1×PBS (pH 6-8) reaching a concentration of 10%, respectively. The two solutions each containing a different PEG component were then mixed together. Similarly, for preparation of silk-PEGs based samples referred to as "X % silk-PEGs" (with X representing the value of the silk concentration), silk fibroins were dissolved in 1×PBS (pH 6-8) reaching a concentration of X %, and then 4-arm PEG-SH and 4-arm PEG-maleimide were each dissolved in the X % silk fibroin solution, with a final concentration of each PEG component reaching 10% of the total solution. The two silk solutions each containing a different PEG component were then mixed together.

Gelation was assessed by a modified test tube inversion method. See Shu et al., 3 Biomacromol. 1304-11 (2002). Specifically, a gel was considered formed when there was no observation of material fluidity or liquid accumulation at the bottom of the inverted vial/tube after mixing two or more components. The mixing of solutions was achieved by brief vortexing at room temperature.

To assess beta sheet formation, samples were incubated at 37° C. covered with 1×PBS (pH 7.4) or treated with an alcohol, e.g., absolute ethanol, for 15 minutes, and analyzed by FTIR (Equinox 55 ATR-FTIR, Bruker Optics Inc., Billerica, Mass.).

TABLE 1

Preparation of Exemplary Silk-PEG Material Formulations

| | Solution A | | Solution B | | Final Composition (mix of 1:1 Volume Ratio of Solution A and Solution B) | |
|---|---|---|---|---|---|---|
| Sample | 4-Arm PEG-Thiol (% w/v) | Silk Fibroin (% w/v) | 4-Arm PEG-Maleimide (% w/v) | Silk Fibroin (% w/v) | Total PEG (Thiol + Maleimide) (% w/v) | Silk Fibroin (% w/v) |
| Control | 10 | — | 10 | — | 10 (5 + 5) | — |
| 5% Silk | 10 | 5 | 10 | 5 | 10 (5 + 5) | 5 |
| 10% Silk | 10 | 10 | 10 | 10 | 10 (5 + 5) | 10 |
| 20% Silk | 10 | 20 | 10 | 20 | 10 (5 + 5) | 20 |

TABLE 2

Final Composition of Exemplary Silk-PEGs Material Formulations.

| Sample Name | 4-arm PEG-SH (wt %) | 4-arm PEG-maleimide (wt %) | Silk fibroin (wt %) |
|---|---|---|---|
| CONTROL (PEGs) | 10% | 10% | — |
| 3% silk-PEGs | 10% | 10% | 3% |
| 5% silk-PEGs | 10% | 10% | 5% |
| 6% silk-PEGs | 10% | 10% | 6% |
| 10% silk-PEGs | 10% | 10% | 10% |
| 20% silk-PEGs | 10% | 10% | 20% |

COSEAL Preparation:

COSEAL was prepared according to the manufacturer's instructions. The kit contained two synthetic polyethylene glycols (PEGs) provided as powder in a syringe, and a liquid pouch containing two syringes—one with a dilute hydrogen chloride solution and one with a sodium phosphate/sodium carbonate solution. The two syringes containing the liquids were supplied pre-assembled into a housing designed to allow mixing of the powder syringe with the correct liquid (e.g., the buffer solution). The liquid was then transferred into the powder by forcefully depressing the plunger. The contents were mixed back and forth between the syringes at least 20 times, until the solid was completely dissolved. The syringe with the dissolved powder and the one containing the other liquid (e.g., dilute hydrochloric acid solution) were then placed into a provided epoxy-like adaptor that allowed the simultaneous dispersion of the two solutions. Cros slinking and gelation of the dispersed liquids would occur within 5-10 s.

Swelling Ratio Determination:

Silk-PEGs based gels were precast in Transwell® inserts with 8 μm pore membranes (Corning Inc., Corning, N.Y.) (e.g., to ensure maximum surface access to solvent), weighed, and then covered with 1×PBS (pH 7.4). Plates containing gel samples were then incubated at 37° C. and at 50 rpm. At intervals, the buffer solution in gel samples was decanted, and the gels were blotted to remove excess solvent. The remaining gels with inserts were then weighed.

In Vitro Degradation:

Silk-PEGs based gels were prepared similarly as the procedures for preparing the silk-PEG based gels for the swelling ratio determination. The volumes were increased to allow for detection of subtle changes in gel weight. Degradation was determined by incubating 0.1 mL precast gels in 1×PBS (pH 7.4) with or without 1 mg/ml (5 U/mg) Protease XIV (Sigma-Aldrich, St. Louis, Mo.) at 37° C. and 50 rpm. The degradation of gel materials was then determined by daily weighing the gels after incubation for about 10 days to two weeks.

Adhesion Tests:

Dynamic Mechanical Analyses (DMA) in multiple extension mode (MEM) using an RSA III from TA Instruments (Delaware, U.S.A.) were performed to assess and compare the adhesion of COSEAL® and silk-PEGs based biomaterials to intestines or steel. For all the measurements, the gap between fixtures was set to 1 mm and the maximum allowed pull force was 2 g or 0.05 N. The steel fixtures used were 8 mm in diameter. For all runs, the sample equilibration steps were followed by a strain-controlled dynamic time sweep test at low strain amplitude (1%-5% strain at 1 Hz). Following, a transient tensile test at a constant transducer speed of 5 mm/min was collected until complete material-substrate seal failure. Three replicates were averaged to characterize the adhesion of each sample. Sausage casing was used for measuring adhesions of COSEAL® or silk-PEG-based biomaterials to the intestinal mucosa. Sausage casing for the measurements was obtained from Whole Foods Market (Woburn, Mass.), cut into small rectangles, which were then applied onto the steel plates. All tests were done at room temperature, regular humidity with tissue samples kept in sterile PBS until needed for the experiment. The tissue sections were handled and cut in wet state (in the presence of PBS), then applied onto the fixture and allowed to set for 30 s to 1 min prior to testing.

Cytocompatibility Assay:

Primary human cervical fibroblasts passage 8 ($3\times10^5$ cells/well) were cultured under serum-free conditions on tissue culture plates. The wells were coated with PEG-only hydrogels and 10% silk-PEGs hydrogels (shown in Table 1 or 2) prepared in 1×PBS (pH 6). Plates containing gel samples were then incubated for 48 h at 37° C./5% $CO_2$. Cell viability was assessed by using a LIVE/DEAD® Cell Viability Assays (Invitrogen, Carlsbad, Calif.). Images were collected with a fluorescent microscope (Leica Microsystems, Wetzlar, Germany) at 100× magnification.

Subcutaneous Injections:

Samples (200 μL each) were injected subcutaneously into the back of BALB/c mice (n=4) and followed for local tissue reactions and degradation times for 2 weeks. Tissues from injection sites were processed for histological evaluation and stained with hematoxylin and eosin (H&E). Animal studies were conducted in accordance with Tufts IACUC approved protocols.

Statistical Analysis:

Values, represented as mean±standard deviation (S.D.) were compared using Student's t-test (2-tailed, type 3), with $p<0.05$ or $p<0.01$ considered statistically significant and $p<0.005$ considered highly significant. For multiple data comparison, ANOVA Single Factor analysis was used.

Example 2

Gel Formation and Beta-Sheet Content Determination

Figure 1B:
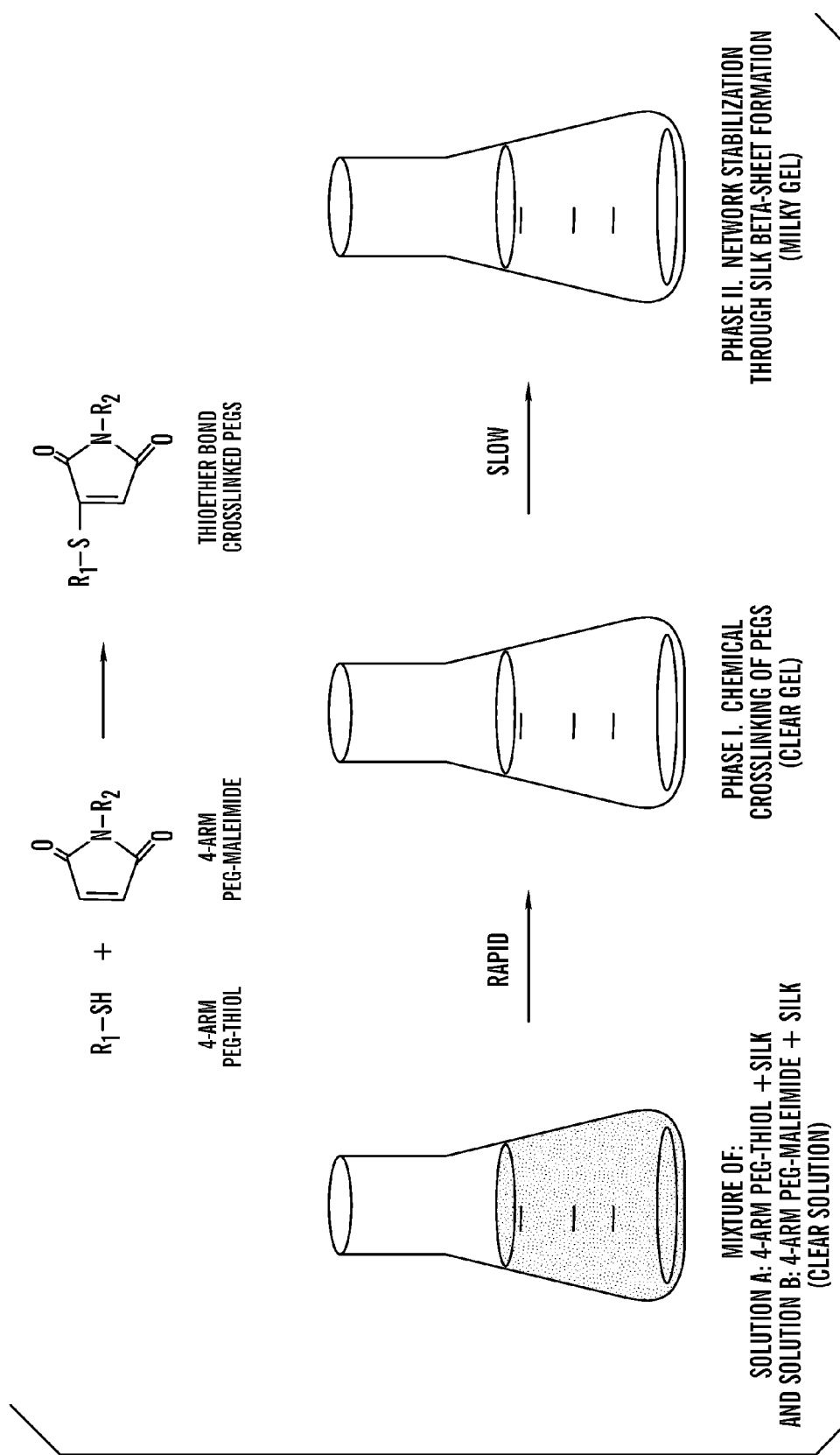
Figure 2:
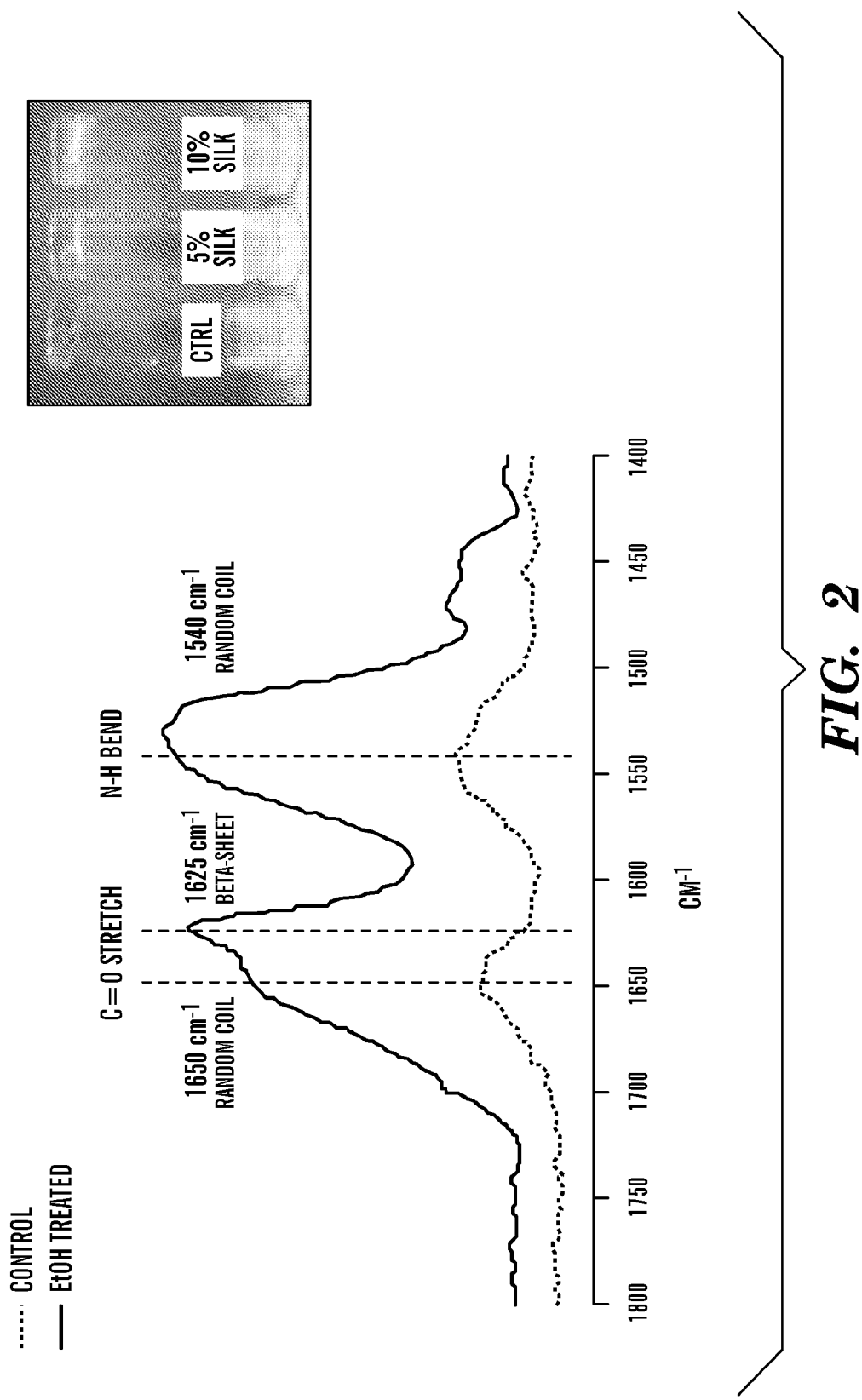
FIG. 2 shows the results in confirmation of the two-step crosslinking model, including a rapid chemical crosslinking step (inset) and a beta-sheet formation by silk (for example, 10% silk-PEG samples were treated with ethanol (EtOH) to assess the β-sheet forming capability of silk fibroin in the silk-PEG blended formulation).

Various formulations for silk-PEGs based hydrogel were obtained as described in Table 1 or 2. A two-step gelation process can occur to form the crosslinked polymer matrix, as shown in FIG. 1A or 1B. The first phase can involve rapid gel formation via chemical reaction between the two PEGs. This step was confirmed by gel formation within seconds upon mixing two samples each containing 4-arm PEG-SH and 4-arm PEG-maleimide, respectively, and this step of gel formation occurred in the presence or absence of silk in the samples (Vanderhooft et al., 8 Biomacromolecules 2883-89 (2007)) (inset of FIG. 2).

To assess the beta-sheet formation of silk in the blended PEG formulations, control (PEGs only) and silk-containing (10% silk-PEGs) samples were treated with ethanol (known as an exogenous accelerator to induce beta-sheet formation) and monitored by FTIR, using the control sample as background. The appearance of the characteristic beta-sheet peak (1625 $cm^{-1}$) was observed as a result of alcohol treatment (e.g., ethanol treatment), indicating that silk fibroin in the blended formation maintained its ability to form beta-sheets (FIG. 2), and that the resulting silk-PEGs crosslinked polymer matrix is further stabilized by the beta-sheet formation of silk fibroin. Under physiological conditions (without alcohol treatment), no beta-sheet was detectable in the control sample (PEGs only) or in the silk-containing samples (e.g., 10% silk-PEG) after 24 hours, indicating that the additional network stabilization through the beta-sheet formation of silk occurs slowly in time (data not shown), if occurring at all. To be noted, ethanol was not used in the experiments described in the Examples below.

Example 3

Biocompatibility of the Silk-PEGs Based Biomaterials

Figure 3B:
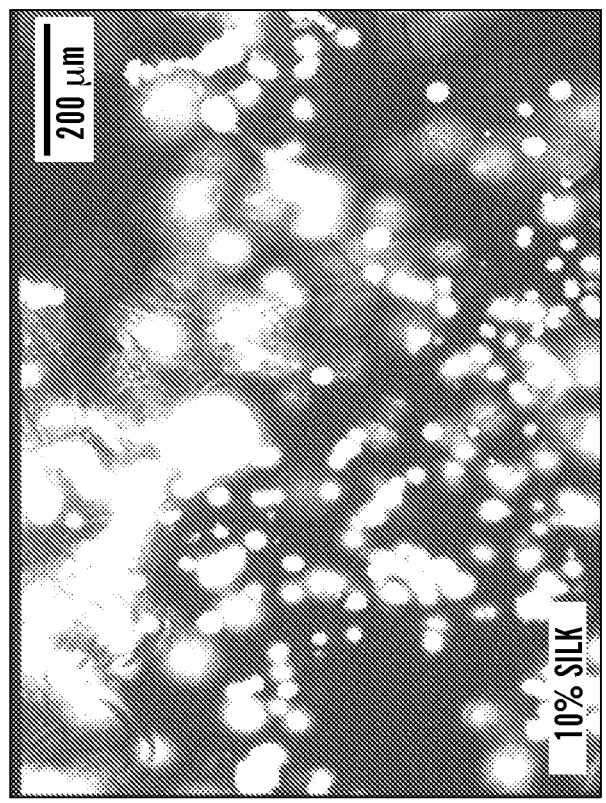
FIGS. 3A-3B show images of the cells cultured with the PEG or PEG-silk-based biomaterials.
Figure 3A:
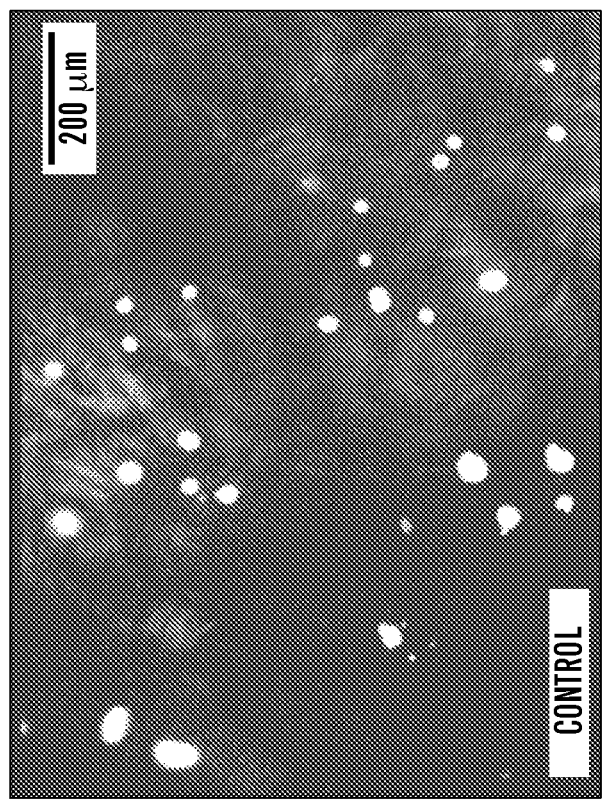

The biocompatibility of the silk-PEGs crosslinked polymer matrix was assessed by casting the silk-PEGs gels and seeding them with cells without prior washing. Such experimental conditions can closely mimic situations where the different components (silk, different PEG components) in the matrix-forming composition would crosslink in vivo without additional washing steps. Primary cervical fibroblasts cultured for 48 hours on the control sample and silk-PEGs samples showed high viability but displayed a rounded morphology on both materials, consistent with published data on silk matrix (Sofia et al., 2001) (FIGS. 3A-3B). This morphology can be explained by, for example, lack of cell-specific attachment sites on the polymer matrix. Such property of the materials can be used for surgical cytoadherence prevention and scar tissue formation prevention in vivo. As shown in FIGS. 3A-3B, the overall cell number on both the control sample and the silk-PEGs materials were similar. Considering that the imaging fields (FIGS. 3A-3B) were selected based on minimal background fluorescence, the local cell numbers on the control sample and the silk-PEGs materials are not the same.

Example 4

Swelling Behavior of the Silk-PEGs Based Biomaterials

Figure 4A:
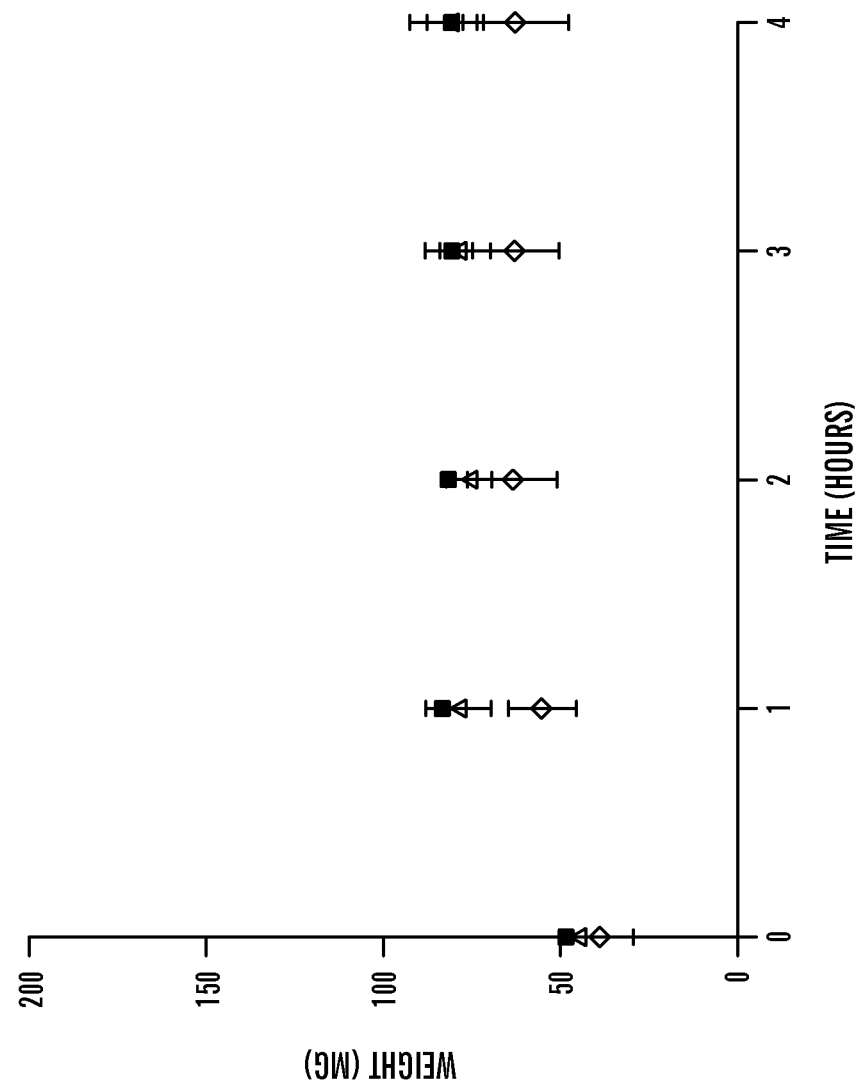
FIGS. 4A-4B show the swelling profiles of silk-PEG based materials containing different concentrations of silk compared to the control PEG.
Figure 4B:
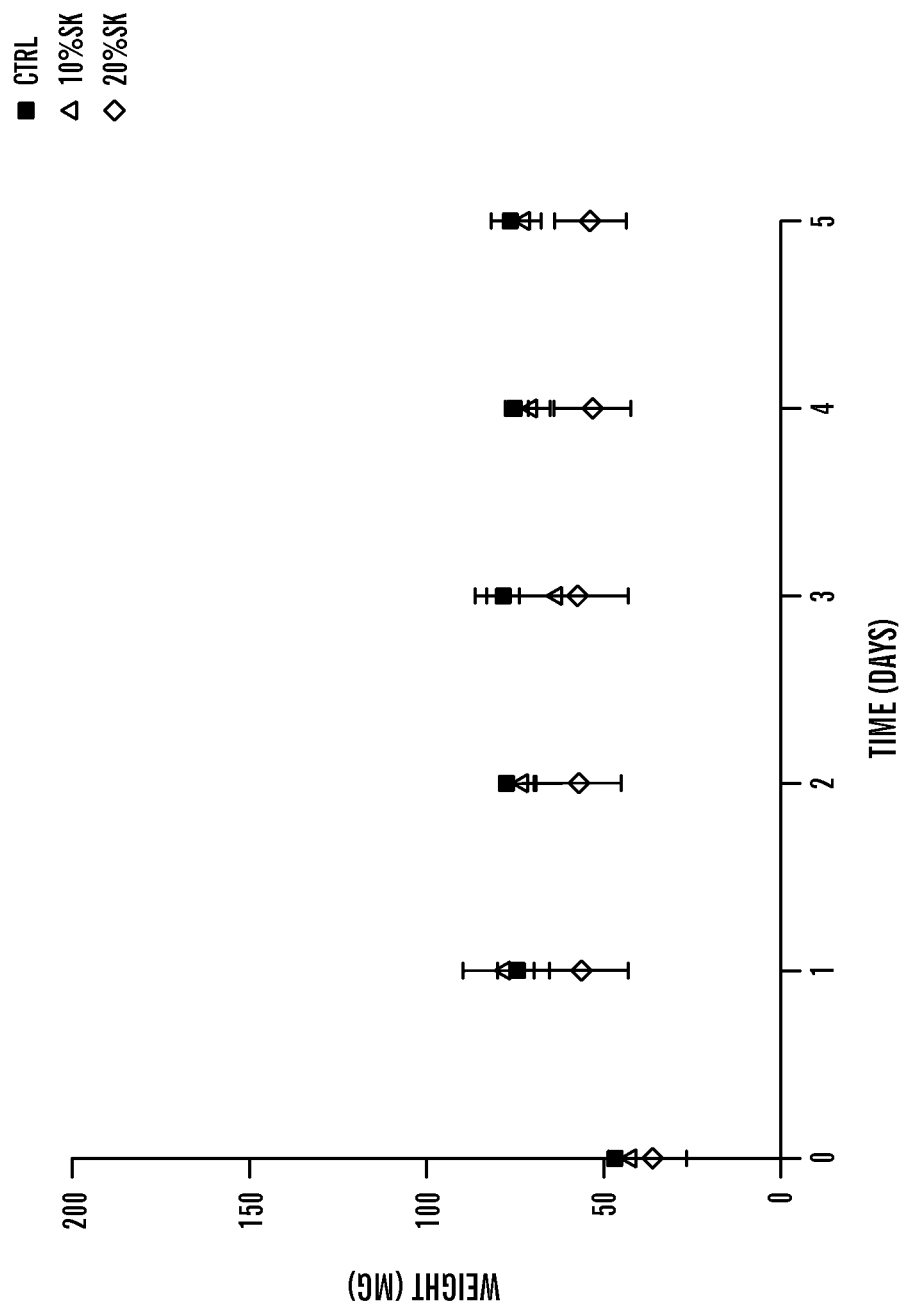

To assess the swelling behavior of the silk-PEGs crosslinked polymer matrix under physiological conditions, samples were cast in Transwell® inserts, covered with buffered saline solution and incubated at 37° C. with gentle shaking. Within 2 h, the control sample (PEG-only) and 10% silk-PEGs sample swelled up to ~70% of their original size, while the 20% silk-PEGs sample only swelled up to ~60% (FIGS. 4A-4B). Sample swelling was monitored for up to day 5 of incubation, and no variations from the initially observed values was further observed. The difference in the swelling ratio between the 10 and 20% sample can be related to the sample formulation and swelling assay setup. Samples were dissolved in water, e.g., deionized water, but assayed for swelling in PBS to mimic physiological conditions. The 20% silk samples have less water compared to the 10% silk sample—therefore upon ionic equilibration the end weight values for the 10% samples were higher than for the 20% ones.

Example 5

Stability and Degradability of the Silk-PEGs Based Biomaterials

Figure 5A:
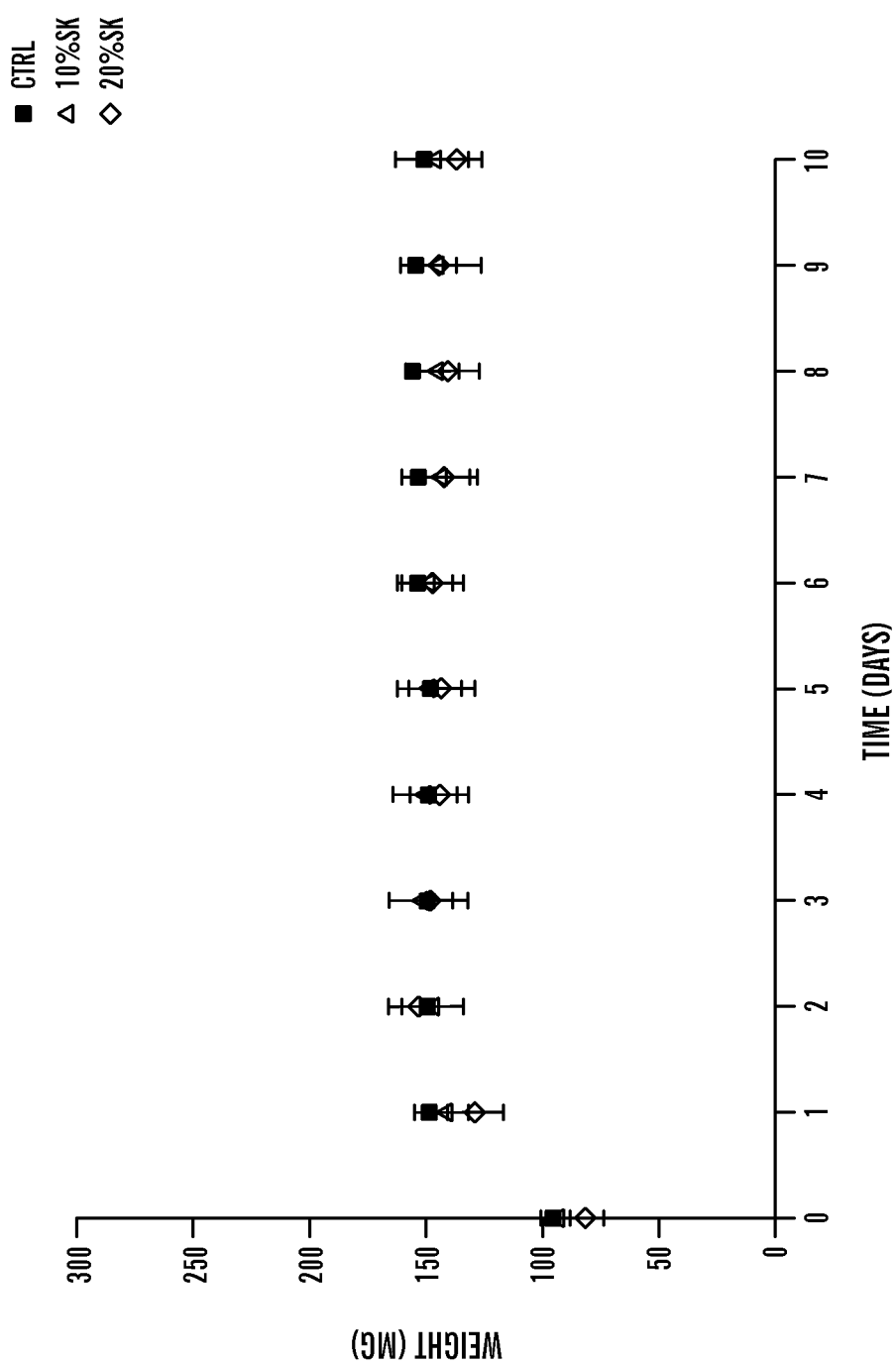
FIGS. 5A-5B show results of in vitro degradation of silk-PEG based biomaterials containing different concentrations of silk compared to the control PEG.
Figure 5B:
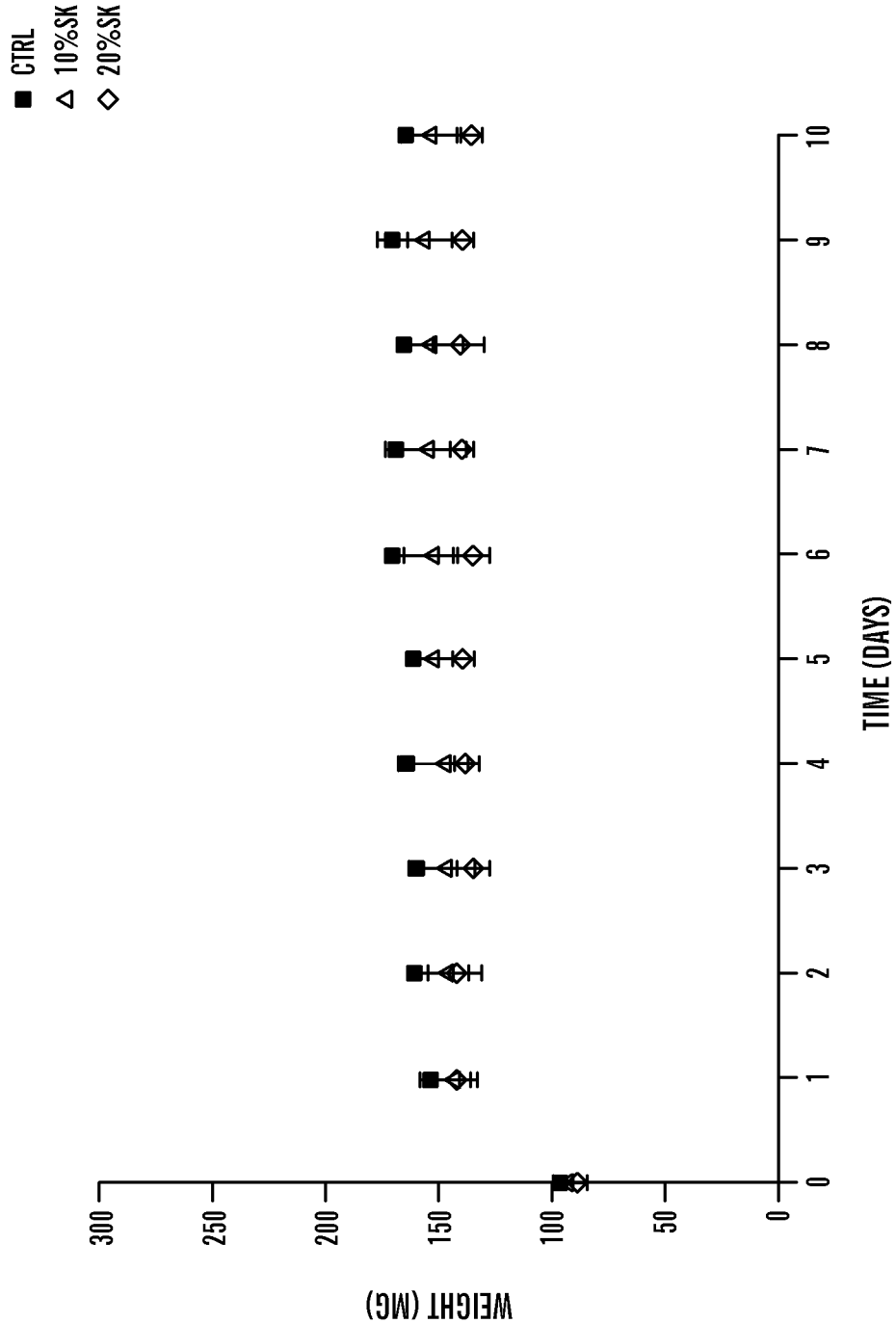

The stability of the silk-PEGs crosslinked polymer matrix was also assessed, by conducting degradation experiments in the presence and absence of Protease XIV. Since mammalian systems do not express silk-specific degrading enzymes, Protease XIV has been generally used as a hallmark silk degrading enzyme. Horan et al. Biomaterials 26: 3385 (2005). Dry-weight degradation of the samples was avoided, since the wet-state scenario is more pertinent to the events occurring in vivo. Degradation was monitored and degradation percent was determining by normalizing the final recorded weight/size to the swollen sample weight/size (the maximum recorded weight/size). Initial swelling of the samples was noticed under both protease-absence control (PBS only) and protease-presence conditions. In the protease-absence control experiment, no significant hydrolytic degradation was noticed during the 14 days experimental process for any of the samples (control (PEGs only), 10% silk-PEGs and 20% silk-PEGs samples) (FIG. 5A). Similarly, in the presence of Protease XIV, no significant enzymatic degradation was noticed during the 14 days experimental process for any of the samples (control, 10% silk-PEGs and 20% silk-PEGs samples) (FIG. 5B), although for lower silk concentrations (3% and 6% w/v) a slight degradation (~10%), consistent with published reports on silk matrix (Horan et al., 26 Biomaterials 3385-93 (2005)), was noticed by day 14. These results indicate that the silk-PEGs hydrogels would degrade very slowly in vivo and would be present for months before degradation. Horan et al., 2005. This material feature can ensure that wound healing can occur completely before the disappearance of the tissue adhesive at wounded sites.

Example 6

Adhesive Properties of the Silk-PEGs Based Biomaterials

Figure 6A:
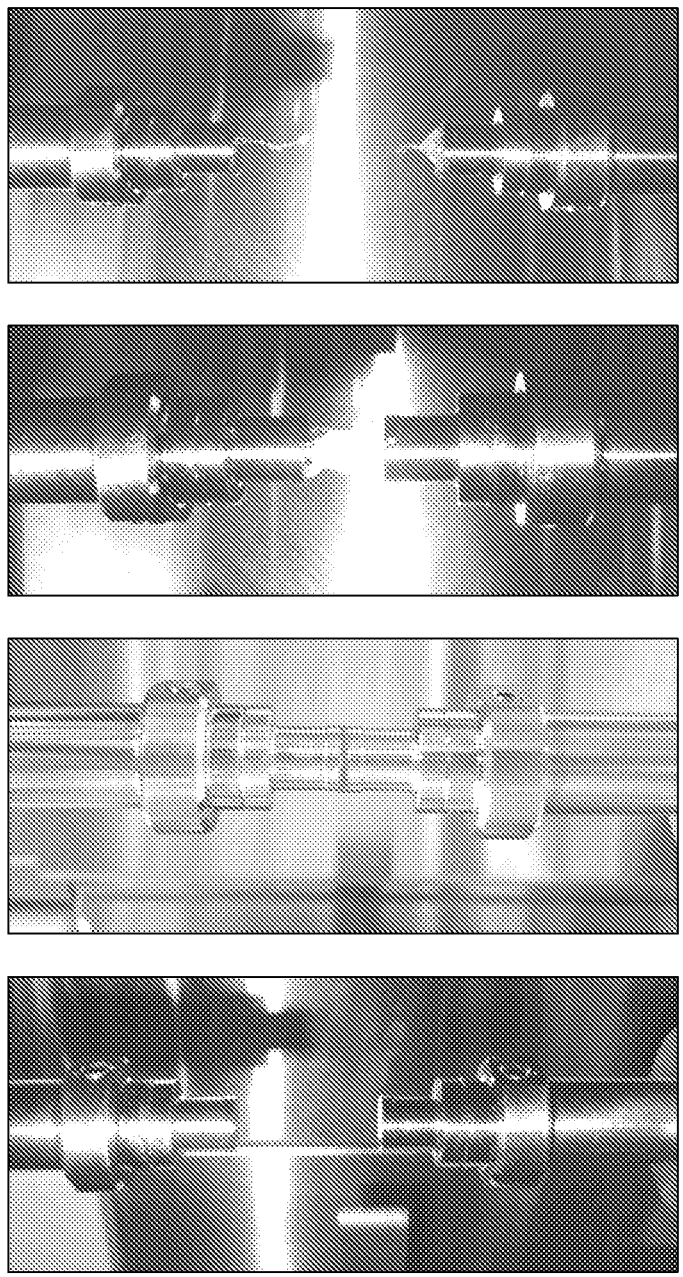
FIGS. 6A-6C show results of the adhesion tests and the corresponding setup.
Figure 6B:
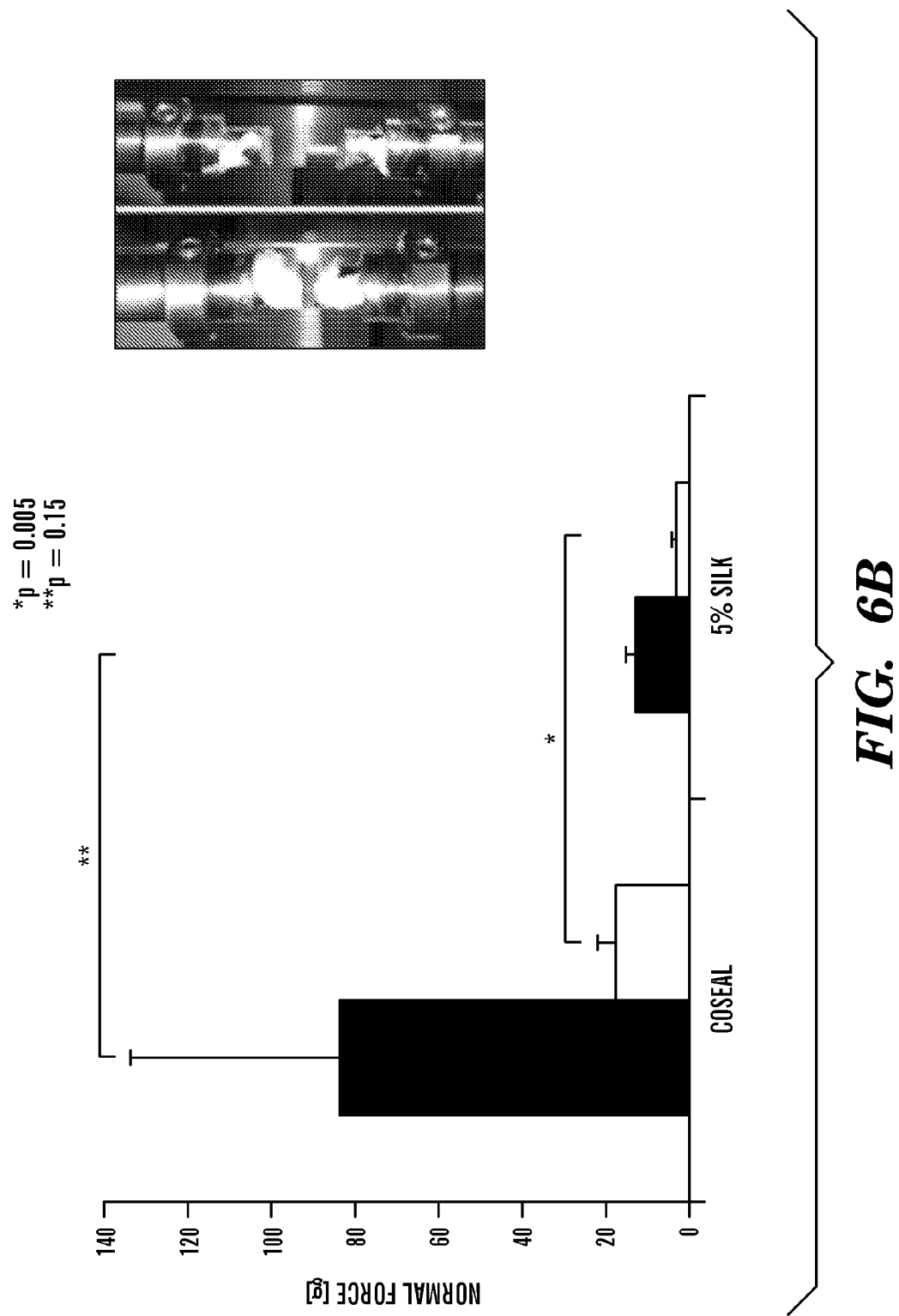
Figure 6C:
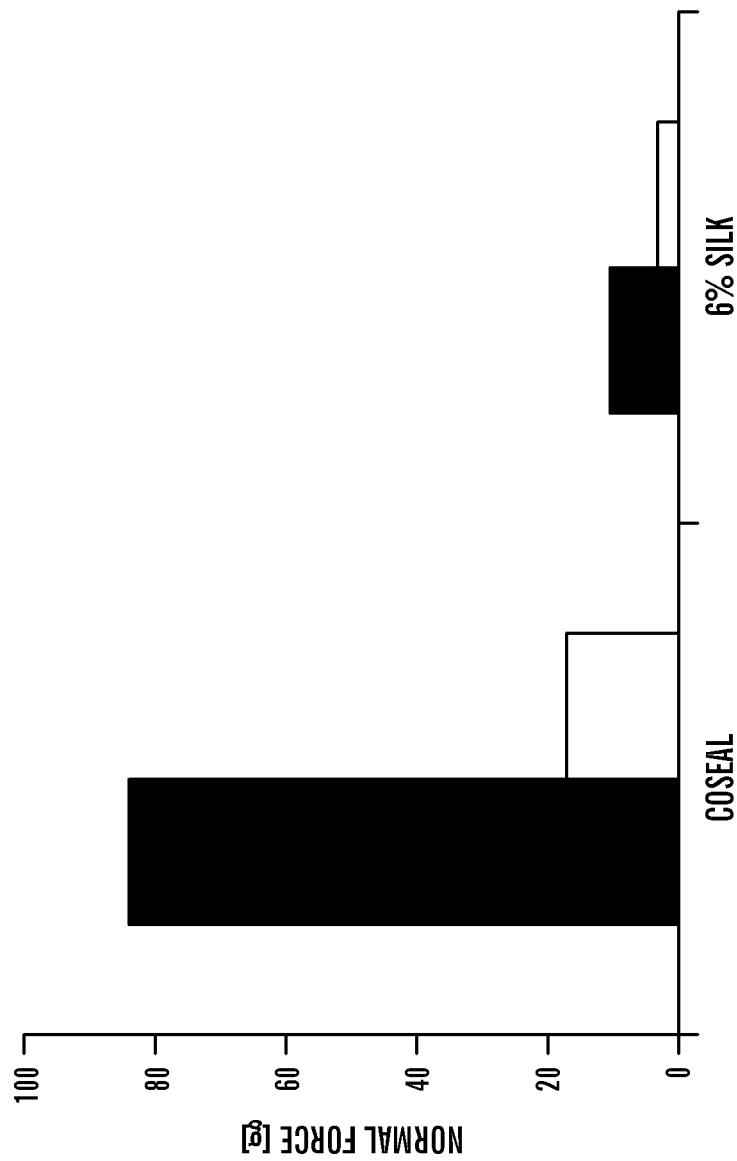

The adhesive capabilities of the silk-PEGs crosslinked polymer matrix were compared to COSEAL® in DMA measurements. The adhesiveness of the silk-PEG materials can be determined based on the pull force needed to break the contact between the sealant and the substrate, e.g., using the setup shown in FIG. 6A. Bovine intestines (sausage casing) were used as biological membrane model for adhesion. However, the biological membrane is highly perishable and inconvenient to handle. Since steel is a more user-friendly alternative to intestines, adhesion trends obtained on the intestines were compared with adhesion trends obtained on steel. While the overall adhesion values were much lower (approximately 8-fold for both COSEAL® and silk-containing samples) on steel than on intestine, the results showed that similar adhesion trend on both substrates can be found for COSEAL® and silk-PEGs gels (FIGS. 6B-6C). Therefore, steel can be used as the substrate for comparing the adhesive properties of COSEAL® and silk-PEGs gels.

Figure 7A:
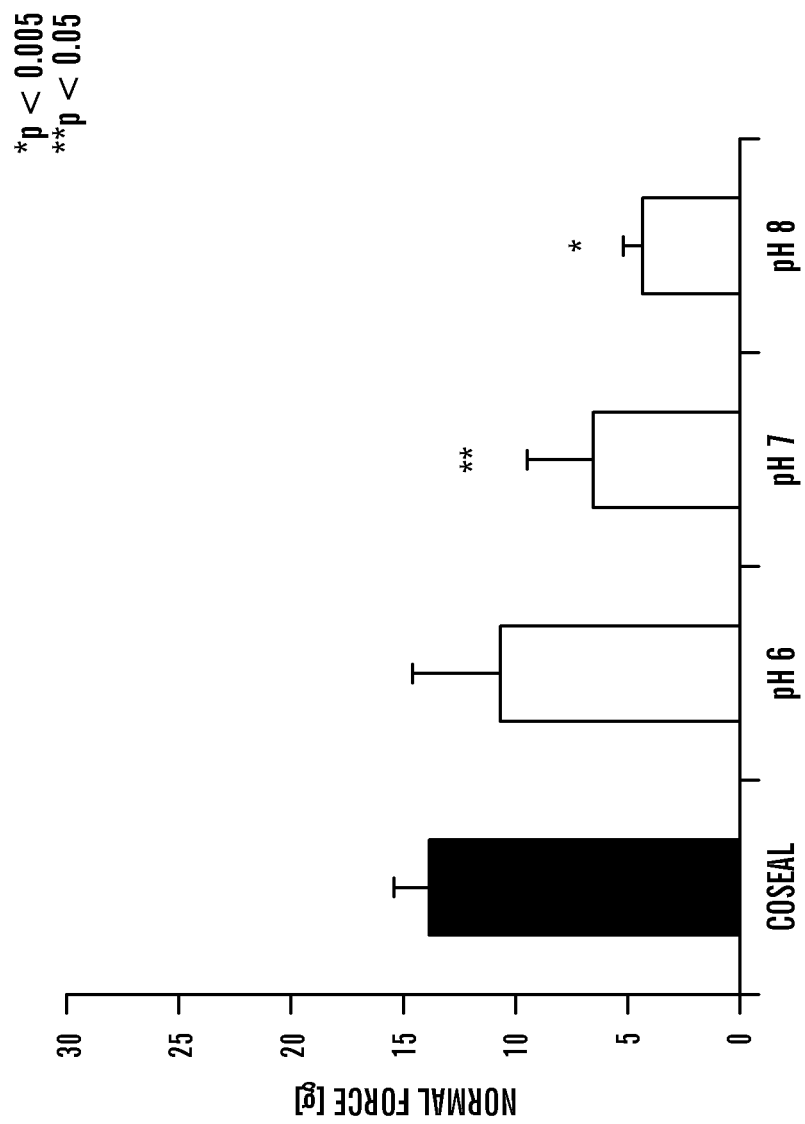
FIGS. 7A-7E show the results of DMA measurements to characterize the adhesion of silk-PEGs based biomaterials.

Without wishing to be bound by theory, since the chemical reaction between the thiol and maleimide functionalities present on the PEGs is pH sensitive (basic pH values would favor the formation of disulfide bonds rather than thioether), it was next sought to determine the pH dependence of the adhesion for the silk-containing PEG samples (e.g., 10% silk-PEG samples) and controls. It was determined that one of the components in COSEAL® has a slightly acidic pH value, which is neutralized to ~7, after the two components of COSEAL® are mixed. The pH values tested for silk-PEGs material preparation were within the physiological range (6.0-8.0), and silk-PEGs materials prepared at 1×PBS pH 6.0 presented higher adhesive properties. For silk-PEGs samples prepared in pH 6 (1×PBS), the adhesion values to steel were comparable to that of COSEAL®, while for silk-PEGs samples prepared in pH 7 or pH 8 buffers, the adhesion values to steel were surpassed by COSEAL® (FIG. 7A). In some embodiments, the PBS used herein does not contain divalent ions, such as calcium ions. After silk-PEGs materials were chemically crosslinked, no pH-dependence of beta-sheet formation was detectable (data not shown), indicating that the pH value can have a larger impact on the chemical crosslinking step rather than the physical crosslinking step (e.g., beta-sheet formation). It is believed that lower pH can help preserve the free thiol functional groups for the 4-arm PEG-SH, i.e., the lower pH prevents thiols from forming intra- or inter-molecular disulfide bonds which would reduce 4-arm PEG-SH's capability to react with the maleimide functional groups of 4-arm PEG-maleimide.

Figure 7B:
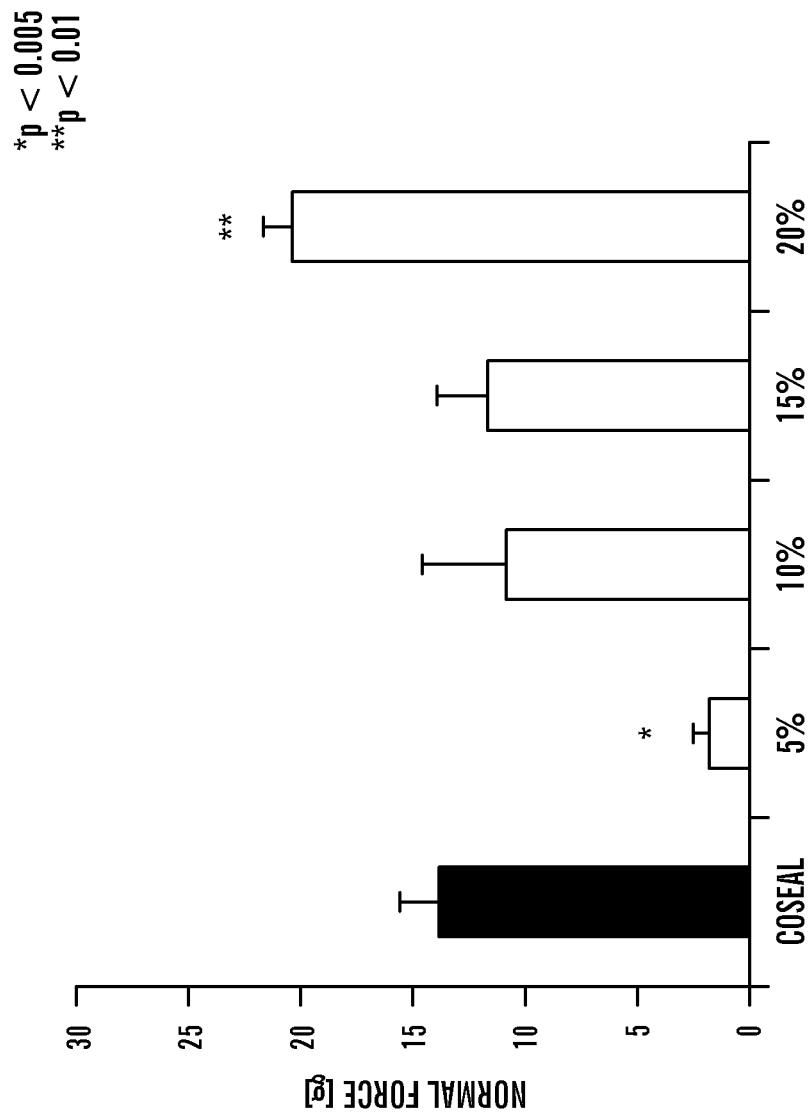

The effect of silk concentration on adhesion capabilities of the silk-PEGs crosslinked polymer matrix was also analyzed. Comparable adhesion values were obtained for COSEAL®, 10% silk-PEGs and 15% silk-PEGs samples. Lower adhesion (p<0.005) was observed for the 5% silk-PEGs sample, while the 20% silk-PEGs sample outperformed COSEAL® (p<0.01) with approximately 50% increase in adhesiveness (FIG. 7B). These results appear to indicate that silk-PEGs crosslinked polymer matrix, containing 10% w/v or higher of silk fibroin, can be more suitable for applications as a tissue sealant.

Figure 7C:
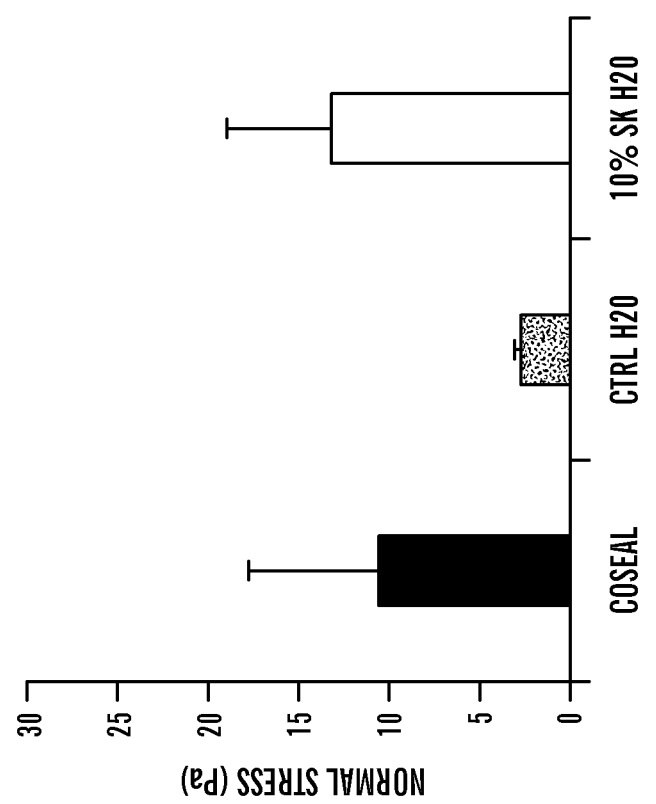
Figure 7D:
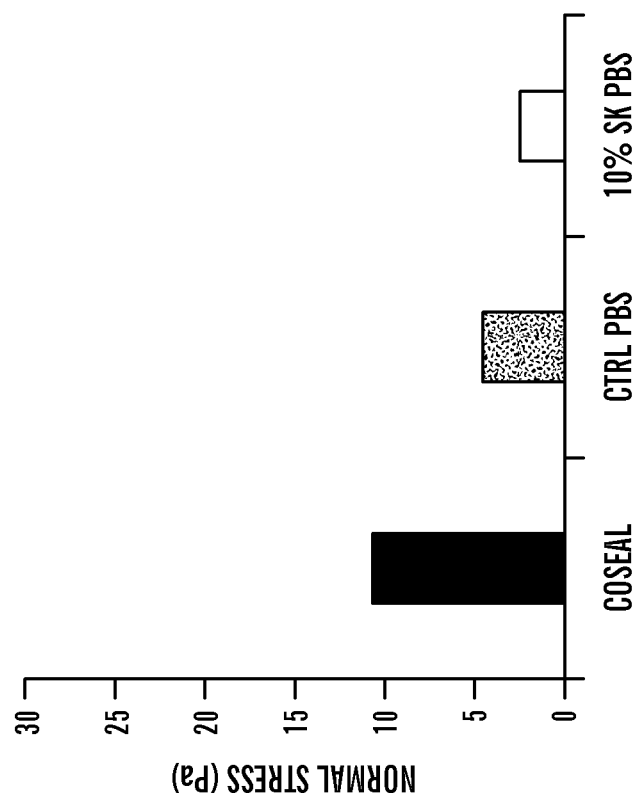
Figure 7E:
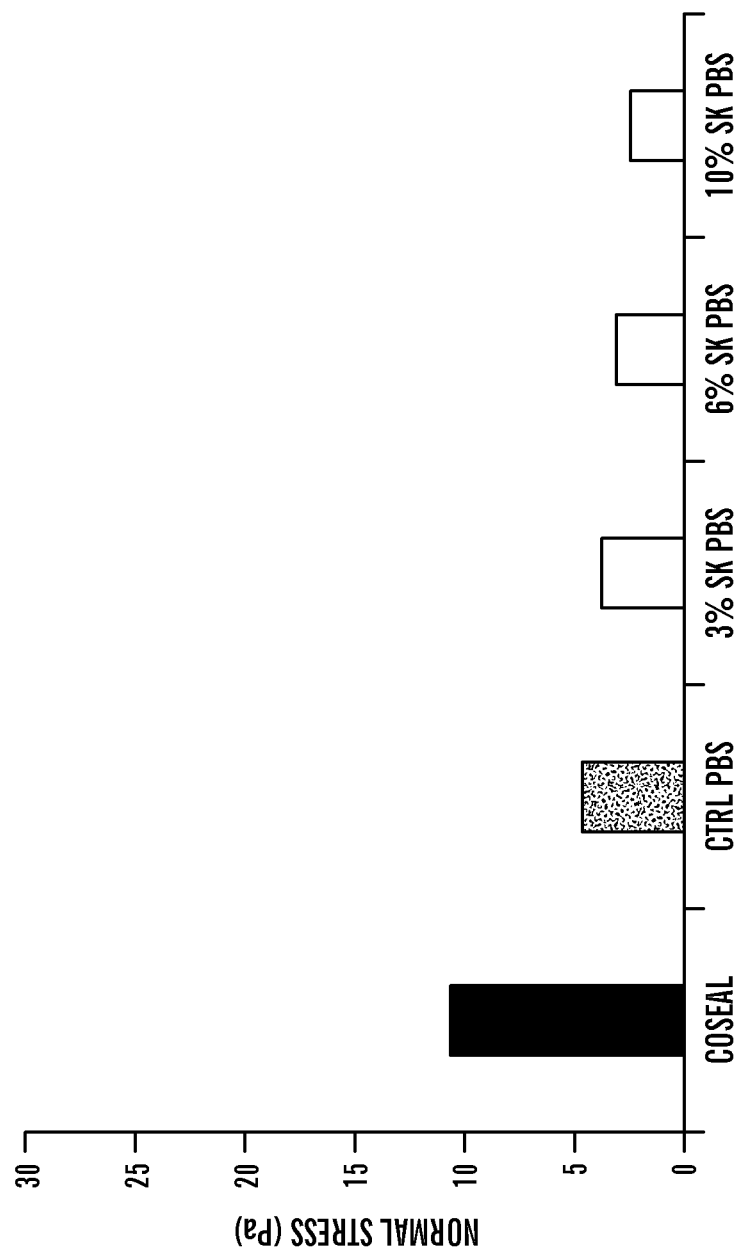
Figure 8A:
FIGS. 8A-8B show hematoxylin and eosin (H&E) staining images of tissue samples subcutaneously injected with either COSEAL® (FIG. 8A) or 5% silk-PEG (FIG. 8B) samples two weeks post-procedure. Black arrows indicate the injected material. White arrows indicate similar levels of fibrosis in the two samples, consisted with previously-reported data on COSEAL® (See Wallace et al., J Biomed Mater Res. 58: 545 (2001)).
Figure 8B:
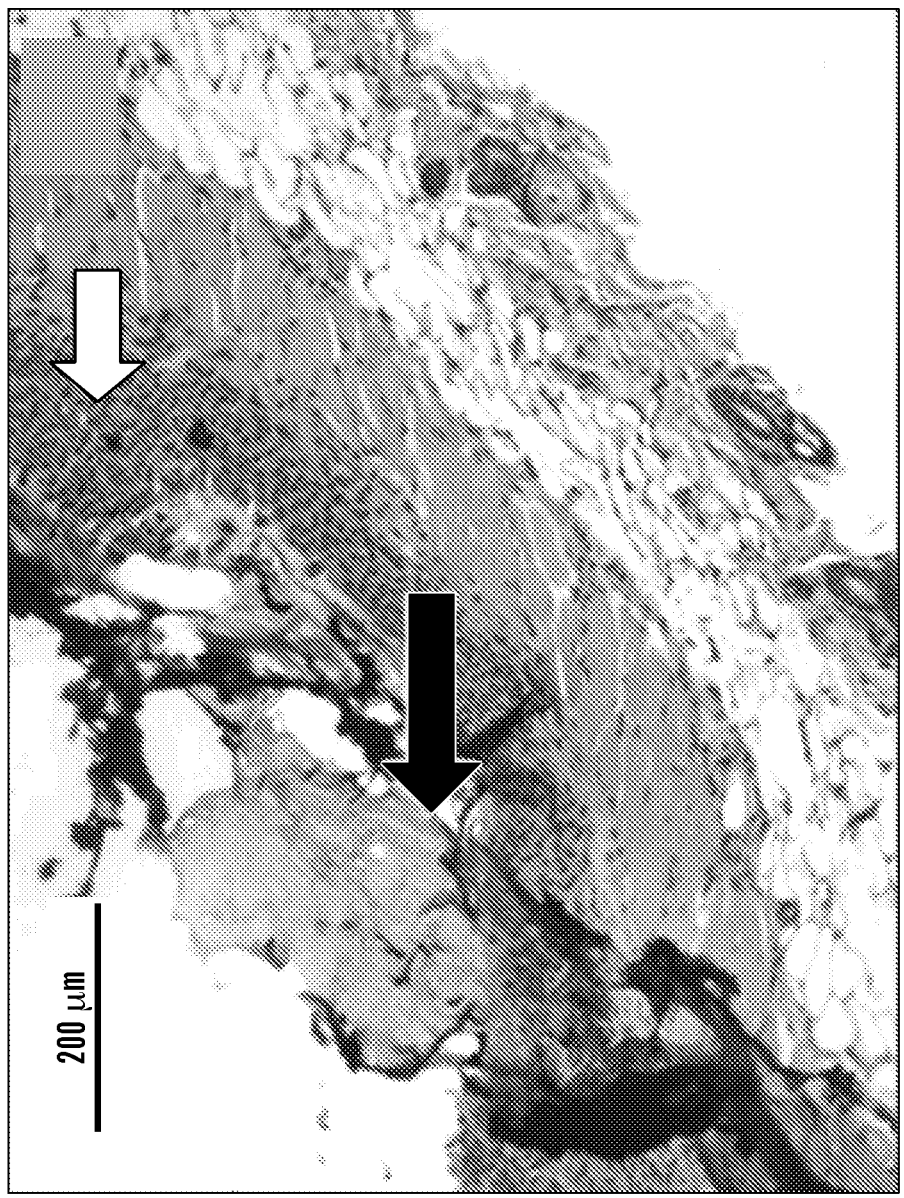

To assess the effects of solvent on the adhesive capabilities of the silk-PEG materials, samples were prepared in 1×PBS containing divalent ions such as calcium ions (pH 7.4) or in water (e.g., deionized water) for evaluation purposes. For all formulations indicated (control, 3% silk, 6% silk and 10% silk) CoSeal showed better adhesion to steel (normal stress of approximaterly 10 Pa for CoSeal versus 2 Pa-4 Pa for all other samples) (FIGS. 7D-7E). However, samples prepared in water (e.g., deionized water) showed strong adherence to steel. For example, 10% silk- PEG samples cast in water were assessed and yielded adhesion values to steel comparable to COSEAL® (FIG. 7C). Comparable adhesive properties to COSEAL® on steel were found for the silk-containing PEG samples when 10% silk-containing samples were prepared in water. Thus, the solvents used for silk-PEG sample preparations (e.g., water versus phosphate buffered saline) can affect the adhesive properties of the materials. Without wishing to be bound by theory, the presence of divalent ions in saline, such as $Ca^{2+}$, could induce premature beta sheet formation in silk (see Kim et al. Biomacromolecules. 5:786 (2004)) and decrease material adhesiveness. However, the absence of ions in the water-based samples can change the swelling properties of the materials. Accordingly, in some embodiments, the aqueous solution used for silk-PEG biomaterial preparation can be water, e.g., deionized water. In other embodiments, the aqueous solution used for silk-PEG biomaterial preparation can exclude divalent ions, for example, a buffer system containing only monovalent ions.

Example 7

In Vivo Compatibility of the Silk-PEGs Based Biomaterials

The in vivo compatibility of the silk-PEG blends was assessed. Materials (COSEAL® and silk-PEG based materials, e.g., 5% silk/PEG) were then injected subcutaneously on the back of BALB/c mice and removed for histological analysis after 2 weeks. Both materials integrated well with the native tissue causing no significant inflammatory response and normal levels of fibrosis (FIG. 8), as previously reported for COSEAL®. Wallace et al. J Biomed Mater Res. 58: 545 (2001).

In subcutaneous injections in mice the tissue compatibility of silk-based sealants was comparable to CoSeal. Both materials were still present after 2 weeks. Previous studies reported that in subcutaneous implants of pre-made gels in rabbits, COSEAL® completely degraded or resorbed after ~2 weeks. Wallace et al. J Biomed Mater Res. 58: 545 (2001). The discrepancies noticed in degradation rates can be due to the different experimental conditions (implants vs. injections; pre-made gels vs. in situ crosslinking; rabbits vs. mice). Regardless, the data presented herein indicate that some embodiments of the silk-PEG-based composites can possess hemostatic and/or sealant properties for bleeding control.

REFERENCES

Wheat J C, Wolf J S Jr. Advances in bioadhesives, tissue sealants, and hemostatic agents. Urol Clin North Am 2009; 36:265-275.
Spotnitz W D, Burks S. Hemostats, sealants, and adhesives: Components of the surgical toolbox. Transfusion 2008; 48:1502-1516.
Jenkins H P, Janda R, Clarke J. Clinical and experimental observations on the use of gelatin sponge or foam. Surgery 1946; 20:124-132.
Gill I S, Ramani A P, Spaliviero M, Xu M, Finelli A, Kaouk J H, Desai M M. Improved hemostasis during laparoscopic partial nephrectomy using gelatin matrix thrombin sealant. Urology 2005; 65:463-466.
Lowe J, Luber J, Levitsky S, Hantak E, Montgomery J, Schiestl N, Schofield M, Marra S. Evaluation of the topical hemostatic efficacy and safety of TISSEEL VH S/D fibrin sealant compared with currently licensed TISSEEL VH in patients undergoing cardiac surgery: A phase 3, randomized, double-blind clinical study. J Cardiovasc Surg (Torino) 2007; 48:323-331.
Marcovich R, Williams A L, Rubin M A, Wolf J S Jr. Comparison of 2-octyl cyanoacrylate adhesive, fibrin glue, and suturing for wound closure in the porcine urinary tract. Urology 2001; 57:806-810.
Furst W, Banerjee A. Release of glutaraldehyde from an albuminglutaraldehyde tissue adhesive causes significant in vitro and in vivo toxicity. Ann Thorac Surg 2005; 79:1522-1528; discussion 1529.
Preul M C, Campbell P K, Bichard W D, Spetzler R F. Application of a hydrogel sealant improves watertight closures of duraplasty onlay grafts in a canine craniotomy model. J Neurosurg 2007; 107:642-650.
Torchiana D F. Polyethylene glycol based synthetic sealants: Potential uses in cardiac surgery. Cardiol Surg 2003; 18:504-506.
Wallace D G, Cruise G M, Rhee W M, Schroeder J A, Prior J J, Ju J, Maroney M, Duronio J, Ngo M H, Estridge T, et al. A tissue sealant based on reactive multifunctional polyethylene glycol. J Biomed Mater Res 2001; 58:545-555.
Lin C C, Anseth K S. PEG hydrogels for the controlled release of biomolecules in regenerative medicine. Pharm Res 2009; 26:631-643.
Bini E, Knight D P, Kaplan D L. Mapping domain structures in silks from insects and spiders related to protein assembly. J Mol Biol 2004; 335:27-40.
Hofmann S, Foo C T, Rossetti F, Textor M, Vunjak-Novakovic G, Kaplan D L, Merkle H P, Meinel L. Silk fibroin as an organic polymer for controlled drug delivery. J Control Release 2006; 111:219-227.
Lawrence B D, Marchant J K, Pindrus M A, Omenetto F G, Kaplan D L. Silk film biomaterials for cornea tissue engineering. Biomaterials 2009; 30:1299-1308.
Soffer L, Wang X, Zhang X, Kluge J, Dorfmann L, Kaplan D L, Leisk G. Silk-based electrospun tubular scaffolds for tissue-engineered vascular grafts. J Biomater Sci Polym Ed 2008; 19:653-664.
Sofia S, McCarthy M B, Gronowicz G, Kaplan D L. Functionalized silk-based biomaterials for bone formation. J Biomed Mater Res 2001; 54:139-148.
Zhou C Z, Confalonieri F, Jacquet M, Perasso R, Li Z G, Janin J. Silk fibroin: Structural implications of a remarkable amino acid sequence. Proteins 2001; 44:119-122.
Leisk G G, Lo T J, Yucel T, Lu Q, Kaplan D L. Electrogelation for protein adhesives. Adv Mater 2010; 22:711-715.
Yucel T, Kojic N, Leisk G G, Lo T J, Kaplan D L. Non-equilibrium silk fibroin adhesives. J Struct Biol 2010; 170:406-412.
Vanderhooft J L, Mann B K, Prestwich G D. Synthesis and characterization of novel thiol-reactive poly(ethylene glycol) cross-linkers for extracellular-matrix-mimetic biomaterials. Biomacromolecules 2007; 8:2883-2889.
Shu X Z, Liu Y, Luo Y, Roberts M C, Prestwich G D. Disulfide crosslinked hyaluronan hydrogels. Biomacromolecules 2002; 3:1304-1311.
Chen J, Altman G H, Karageorgiou V, Horan R, Collette A, Volloch V, Colabro T, Kaplan D L. Human bone marrow stromal cell and ligament fibroblast responses on RGD-modified silk fibers. J Biomed Mater Res A 2003; 67:559-570.
Horan R L, Antle K, Collette A L, Wang Y, Huang J, Moreau J E, Volloch V, Kaplan D L, Altman G H. In vitro degradation of silk fibroin. Biomaterials 2005; 26:3385-3393.

Altman G H, Horan R L, Lu H H, Moreau J, Martin I, Richmond J C, Kaplan D L. Silk matrix for tissue engineered anterior cruciate ligaments. Biomaterials 2002; 23:4131-4141.

Kim U J, Park J, Li C, Jin H J, Valluzzi R, Kaplan D L. Structure and properties of silk hydrogels. Biomacromolecules 2004; 5:786-792.

Li C, Vepari C, Jin H J, Kim H J, Kaplan D L. Electrospun silk-BMP-2 scaffolds for bone tissue engineering. Biomaterials 2006; 27:3115-3124.

Nazarov R, Jin H J, Kaplan D L. Porous 3-D scaffolds from regenerated silk fibroin. Biomacromolecules 2004; 5:718-726.

Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of preparing a crosslinked polymer matrix, comprising:
    admixing a composition comprising
        silk fibroin at a concentration of at least 10 wt % of the composition; and
        at least two functionally activated PEG components; and
    crosslinking the composition so that a polymer matrix comprising the silk fibroin in beta sheet form and the PEG components in crosslinked form is prepared.

2. The method of claim 1, wherein beta sheet formation of the silk fibroin is induced via one or more of exposing the mixture to an alcohol treatment, or exposing the mixture to a water-annealing treatment.

3. The method of claim 1, wherein the silk fibroin is depleted of sericin before admixing with the functionally activated PEG components.

4. The method of claim 1, wherein the crosslinked matrix is a hydrogel, a mat, a film, a sponge, a 3-dimensional scaffold, a fiber or any combinations thereof.

5. The method of claim 1, wherein each PEG component is a four-armed PEG.

6. The method of claim 1, wherein one of the PEG components is functionally activated with a maleimidyl group.

7. The method of claim 6, wherein one of the PEG components is functionally activated with a thiol group.

8. The method of claim 1, wherein at least the silk fibroin is in an aqueous solution.

9. The method of claim 8, wherein the aqueous solution excludes divalent ions.

10. The method of claim 8, wherein each PEG component is suspended or dissolved in the silk fibroin solution.

11. The method of claim 10, wherein the pH of the aqueous solution ranges from about 6 to about 8.

12. The method of claim 1, wherein the concentration of each PEG component in the composition ranges from about 2.5 wt % to about 15 wt %.

13. The method of claim 1, wherein the silk fibroin is at a concentration sufficient to yield an adhesive strength of the crosslinked polymer matrix to at least about 10 Pa.

14. The method of claim 1, wherein the composition further comprises an active agent selected from the group consisting of cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, hemostatic agents, and any combinations thereof.

15. A crosslinked polymer matrix produced by the method of claim 1.

16. A tissue sealant or adhesive comprising the crosslinked polymer matrix of claim 15.

17. The method of claim 1, wherein the composition is admixed at a target site of a subject to form a tissue sealant or an adhesive on the target site.

18. The method of claim 17, wherein a surface of the target site is crosslinked with at least one of the components in the composition.

19. The method of claim 17, wherein the subject is an implant, or a tissue or organ.

20. The method of claim 19, wherein the tissue or organ is in the vicinity of pressure sensitive structures, has an open wound or a combination thereof.

21. The method of claim 17, wherein the two PEG components are separately administered to the subject thereby forming the tissue sealant or adhesive in vivo.

* * * * *